United States Patent
Li et al.

(10) Patent No.: US 11,715,566 B2
(45) Date of Patent: Aug. 1, 2023

(54) OPTIMAL MULTI-ELECTRODE TRANSCUTANEOUS STIMULATION WITH HIGH LOCALITY AND INTENSITY

(71) Applicant: THE REGENTS OF THE UNIVERSITY OF CALIFORNIA, Oakland, CA (US)

(72) Inventors: Ying Li, Los Angeles, CA (US); Wentai Liu, Los Angeles, CA (US); Yi-Kai Lo, Los Angeles, CA (US)

(73) Assignee: THE REGENTS OF THE UNIVERSITY OF CALIFORNIA, Oakland, GA (US)

( * ) Notice: Subject to any disclaimer, the term of this patent is extended or adjusted under 35 U.S.C. 154(b) by 970 days.

(21) Appl. No.: 16/432,529

(22) Filed: Jun. 5, 2019

(65) Prior Publication Data
US 2019/0355476 A1    Nov. 21, 2019

Related U.S. Application Data

(63) Continuation of application No. PCT/US2017/064970, filed on Dec. 6, 2017.
(Continued)

(51) Int. Cl.
*A61B 5/055*    (2006.01)
*G16H 50/50*    (2018.01)
(Continued)

(52) U.S. Cl.
CPC ............ *G16H 50/50* (2018.01); *A61B 5/055* (2013.01); *A61B 5/369* (2021.01); *A61B 5/389* (2021.01);
(Continued)

(58) Field of Classification Search
CPC ....... A61B 5/055; A61B 5/369; A61B 5/4848; A61B 6/032; G06F 17/11; G16H 20/40; G16H 30/40
See application file for complete search history.

(56) References Cited

U.S. PATENT DOCUMENTS

2007/0203545 A1    8/2007    Stone
2010/0135553 A1    6/2010    Joglekar
(Continued)

FOREIGN PATENT DOCUMENTS

WO    2010120823 A2    10/2010

OTHER PUBLICATIONS

European Patent Office (EPO), Supplementary European Search Report dated Jun. 20, 2020, related European patent application No. 17878883.2, pp. 1-12, claims searched, pp. 13-17.
(Continued)

*Primary Examiner* — Reginald R Reyes
(74) *Attorney, Agent, or Firm* — O'Banion & Ritchey LLP; John P. O'Banion

(57) ABSTRACT

Methods, apparatus, and systems are disclosed for optimization techniques and a realistic 3D model to design optimal parameters for transcutaneous stimulation to achieve focalized stimulation of a target tissue such as the spinal cord, brain or other internal organ. The methods, apparatus, and systems include generation of a 3D model from a CT/MRI image, as well as an optimization algorithm that enables stimulation of any target location (e.g., on the dorsal root, or on the dorsal column) with any orientation at high precision.

26 Claims, 19 Drawing Sheets

Related U.S. Application Data

(60) Provisional application No. 62/532,477, filed on Jul. 14, 2017, provisional application No. 62/430,490, filed on Dec. 6, 2016.

(51) Int. Cl.

| | |
|---|---|
| *A61N 1/36* | (2006.01) |
| *G16H 20/40* | (2018.01) |
| *G16H 30/40* | (2018.01) |
| *G16H 70/20* | (2018.01) |
| *A61B 5/00* | (2006.01) |
| *A61B 6/03* | (2006.01) |
| *A61N 1/08* | (2006.01) |
| *A61N 1/20* | (2006.01) |
| *G06F 17/11* | (2006.01) |
| *G06F 30/23* | (2020.01) |
| *A61B 5/369* | (2021.01) |
| *A61B 5/389* | (2021.01) |
| *G06F 111/10* | (2020.01) |

(52) U.S. Cl.
CPC ............ *A61B 5/4848* (2013.01); *A61B 6/032* (2013.01); *A61N 1/08* (2013.01); *A61N 1/205* (2013.01); *A61N 1/36003* (2013.01); *A61N 1/36007* (2013.01); *A61N 1/36014* (2013.01); *A61N 1/36031* (2017.08); *G06F 17/11* (2013.01); *G06F 30/23* (2020.01); *G16H 20/40* (2018.01); *G16H 30/40* (2018.01); *G16H 70/20* (2018.01); *G06F 2111/10* (2020.01)

(56) References Cited

U.S. PATENT DOCUMENTS

| | | |
|---|---|---|
| 2011/0106221 A1 | 5/2011 | Neal, II |
| 2011/0137381 A1 | 6/2011 | Lee |
| 2012/0245653 A1 | 9/2012 | Bikson |
| 2014/0067013 A1 | 3/2014 | Kaula |
| 2014/0257047 A1 | 9/2014 | Sillay |
| 2019/0180864 A1* | 6/2019 | Reicher ................. G06T 7/0014 |
| 2019/0184171 A1* | 6/2019 | Mustakos .............. G16H 40/00 |

OTHER PUBLICATIONS

ISA/US, United States Patent and Trademark Office (USPTO), International Search Report and Written Opinion dated Feb. 9, 2018, related PCT international application No. PCT/US2017/064970, pp. 1-7, claims searched, pp. 8-17.

European Patent Office (EPO), Supplementary European Search Report dated May 10, 2023, related European patent application No. 17878883.2, pp. 1-11, claims searched, pp. 12-16.

* cited by examiner

Intensity: 3.62V/m
Focality: 1.75cm

Intensity: 3.42V/m
Focality: 0.95cm

Intensity: 3.02V/m
Focality: 1.18cm

Intensity: 3.06V/m
Focality: 0.83cm

OPTIMAL MULTI-ELECTRODE TRANSCUTANEOUS STIMULATION WITH HIGH LOCALITY AND INTENSITY

CROSS-REFERENCE TO RELATED APPLICATIONS

This application claims priority to, and is a 35 U.S.C. § 111(a) continuation of, PCT international application number PCT/US2017/064970 filed on Dec. 6, 2017, incorporated herein by reference in its entirety, which claims priority to, and the benefit of, U.S. provisional patent application Ser. No. 62/532,477 filed on Jul. 14, 2017, incorporated herein by reference in its entirety, and which claims priority to, and the benefit of, U.S. provisional application Ser. No. 62/430,490 filed on Dec. 6, 2016, incorporated herein by reference in its entirety. Priority is claimed to each of the foregoing applications.

The above-referenced PCT international application was published as PCT International Publication No. WO 2018/106843 on Jun. 14, 2018, which publication is incorporated herein by reference in its entirety.

STATEMENT REGARDING FEDERALLY SPONSORED RESEARCH OR DEVELOPMENT

Not Applicable

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to systems for therapeutic stimulation and imaging, and more particularly to multi-electrode transcutaneous stimulation for therapy and medical imaging.

2. Background Discussion

Epidural spinal cord stimulation (eSCS) has been used for restoration of motor functions in spinal cord injury (SCI), pain management, and spasticity control. However, it is invasive that needs surgery to implant electrodes into the body.

As an alternative, the transcutaneous spinal cord stimulation (tSCS) was used to achieve similar effect as eSCS in a noninvasive way. It has been shown that tSCS is able to elicit the locomotor-like movements in healthy subjects as well as in spinal cord injury (SCI) subjects. tSCS has also been demonstrated to control pain and suppress spasticity. Conventional tSCS uses one or two large electrodes for stimulation, resulting in non-focal current flows in the spinal cord. Due to large activated area, it is difficult to understand the underlying mechanism, for example which part of the activated area contributes to the treatment. Further, the two-electrode montage is not able to target multiple sites simultaneously, which limits its effectiveness. When stimulating different targets, it is often desirable to frequently change the electrode locations. Therefore, it becomes inconvenient for stimulating a neural network dynamically.

More recently, multiple electrode arrays comprising 3*3 electrodes, 3*7 and 3*8 electrodes have been adopted for transcutaneous spinal cord stimulation, which allow multisite stimulation. Compared to single site stimulation, the multisite stimulation has been demonstrated to induce more effective stepping movements and higher amplitude of EMG activity in healthy subjects. However, because their stimulation parameters are just chosen by experience, the induced current is still not focused. In addition, certain sensitive regions such as the bladder can not be avoided. All of these together limit their capability of modulating the neuronal circuits precisely.

To improve the focal accuracy of the stimulation, ring configuration is widely used to enhance the focality of the epidural spinal cord stimulation (eSCS) and transcranial current stimulation (tCS). It is featured by an anode (cathode) electrode surrounding by four cathode (anode) electrodes. Generally, it is good at stimulating the radial orientation, and has difficulty in dealing with tangential orientation. Another limitation lies in that when the target is not underneath any electrode, the ring configuration is not able to stimulate the target precisely. In addition, it is not able to avoid certain regions either.

A more effective and focal stimulation can be achieved by precisely constructing a spinal cord/head model and taking advantage of optimization methods. Several optimization methods have been developed for transcranial direction/alternating current stimulation (tDCS/tACS) as well as deep brain stimulation (DBS). However, there has not been any work that uses optimization methods to obtain higher intensity or focal accuracy for transcutaneous spinal cord stimulation. In tDCS/tACS, the conventional optimization methods either maximize intensity at the target, which results in very low focal accuracy of stimulation (e.g., maximum intensity method), or maximize the focal accuracy at the expense of low intensity (e.g., Linear Constrained Minimum Variance (LCMV)). In addition, in the LCMV method and it variants, a hard constraint is enforced to meet the specified intensity and orientation at the target, which may lead to infeasible solution when the specified intensity is high or the target region is large. In addition, the hard constraint limits the degree of freedom of the problem, which hinders it from obtaining a better solution with higher intensity or focality. Taken together, an optimization method that that is able to always provide a feasible solution, as well as to optimize both intensity and focality at the same time is highly desirable.

Another limitation of conventional optimization methods is that they require the clinician to specify location and intensity at the target, which is usually unknown in most applications. Recently, a method based on the reciprocity principle was proposed, which enables the EEG signal to be used as a guide for designing stimulation patterns without specifying the location of target. However, the stimulation parameters chosen by this method is just empirical, and it is only able to deal with simple situations, such as cases in which a single focal source predominates. It is unable to handle complicated cases, such as multiple targets, spatially extended targets with different orientations in different parts, or containing brain regions to be avoided. In the multiple targets case, it is possible that this method may stimulate the averaged location of these targets. In sum, a better method for guiding the stimulation is needed.

From the hardware perspective, it is a big challenge to control a large number of stimulation channels independently. In addition, the key to a highly spatially focused stimulation is enabling precise control of currents in each stimulation channel. Enabling necessarily high count of independently controlled current sources is challenging.

Thus, in order to use an optimization algorithm to its highest precision, it is highly desirable to have a high channel-count stimulator with precise output current parameters for each channel and seemingly immediate dynamic updates to those parameters in real-time.

BRIEF SUMMARY

One aspect of the present description is a system and method for generation of a 3D model from a CT/MRI image, as well as an optimization algorithm that enables stimulation of any target location (e.g., on the dorsal root, or on the dorsal column) with any orientation at high precision. In addition, the systems and methods of the present description are capable of stimulating not only single target but also multiple targets, as well as avoid certain regions within the anatomy of interest. For hardware, the system provides a hardware platform with capabilities to enable the optimization algorithm to its highest precision: a high channel-count stimulator with precise output current parameters for each channel and seemingly immediate dynamic updates to those parameters in real-time.

One aspect of the present description is a method for optimal and focal transcutaneous spinal cord stimulation.

Another aspect of the present description is a method for transcranial current stimulation.

The systems and methods disclosed herein provide better results than other state-of-the-art methods in terms of directional intensity and focality, and can be extended to stimulation of other internal organs, including the brain.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

Figure 5A:
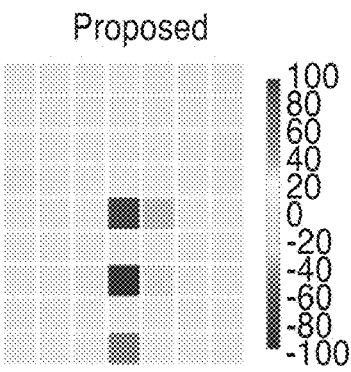
FIG. 5A through FIG. 5C show the stimulation results for the optimization method of the present description, with FIG. 5A showing the electrode weighting (stimulation parameter at each electrode), FIG. 5B showing the intensity E-field at the white matter, and FIG. 5C showing the Directional E-Field in the desired direction (y-axis).
Figure 6A:
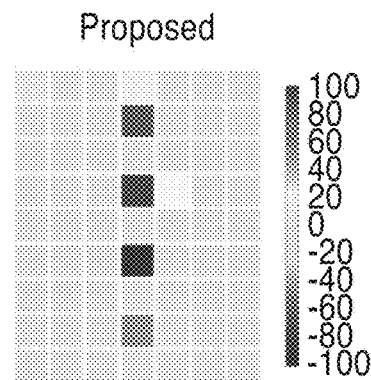
Figure 5B:
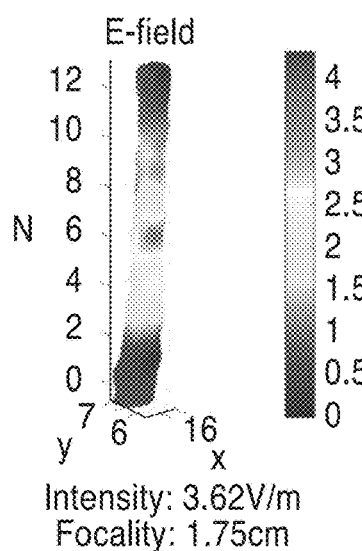
Figure 6B:
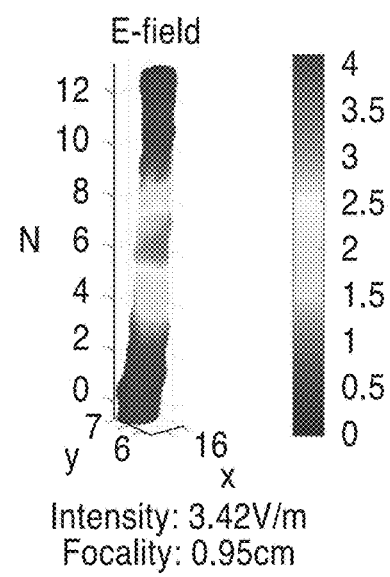
Figure 5C:
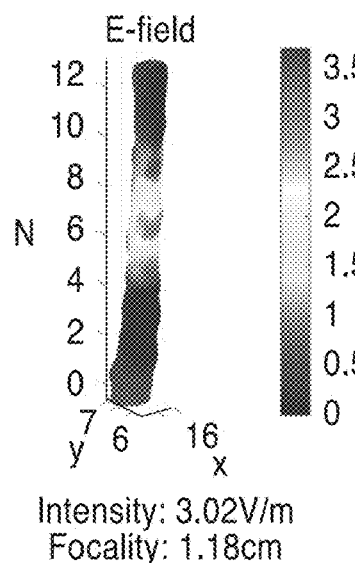
Figure 6C:
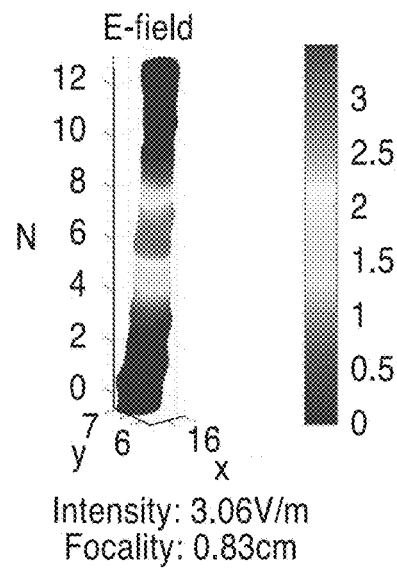

FIG. 6A through FIG. 6C show the stimulation results for the optimization method of the present description for target orientation along the z-axis (tangential to the electrode), with FIG. 6A showing the electrode weighting (stimulation parameter at each electrode), FIG. 6B showing the intensity E-field at the white matter, and FIG. 5C showing the Directional E-Field intensity in the desired direction (z-axis).

Figure 7:
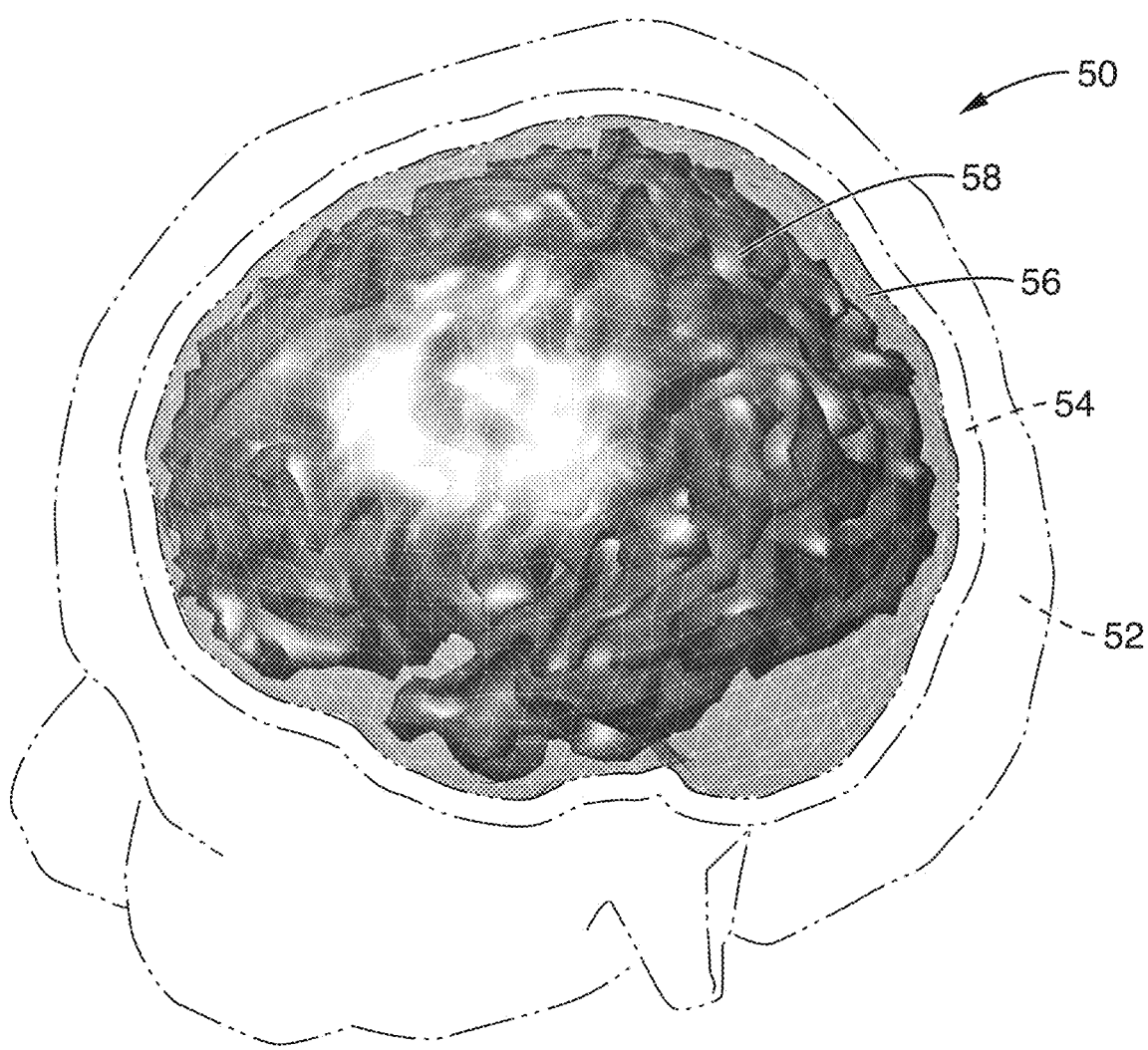

FIG. 7 shows an image of a 3D head model including scalp, skull, CSF, and cortex.

Figure 8:
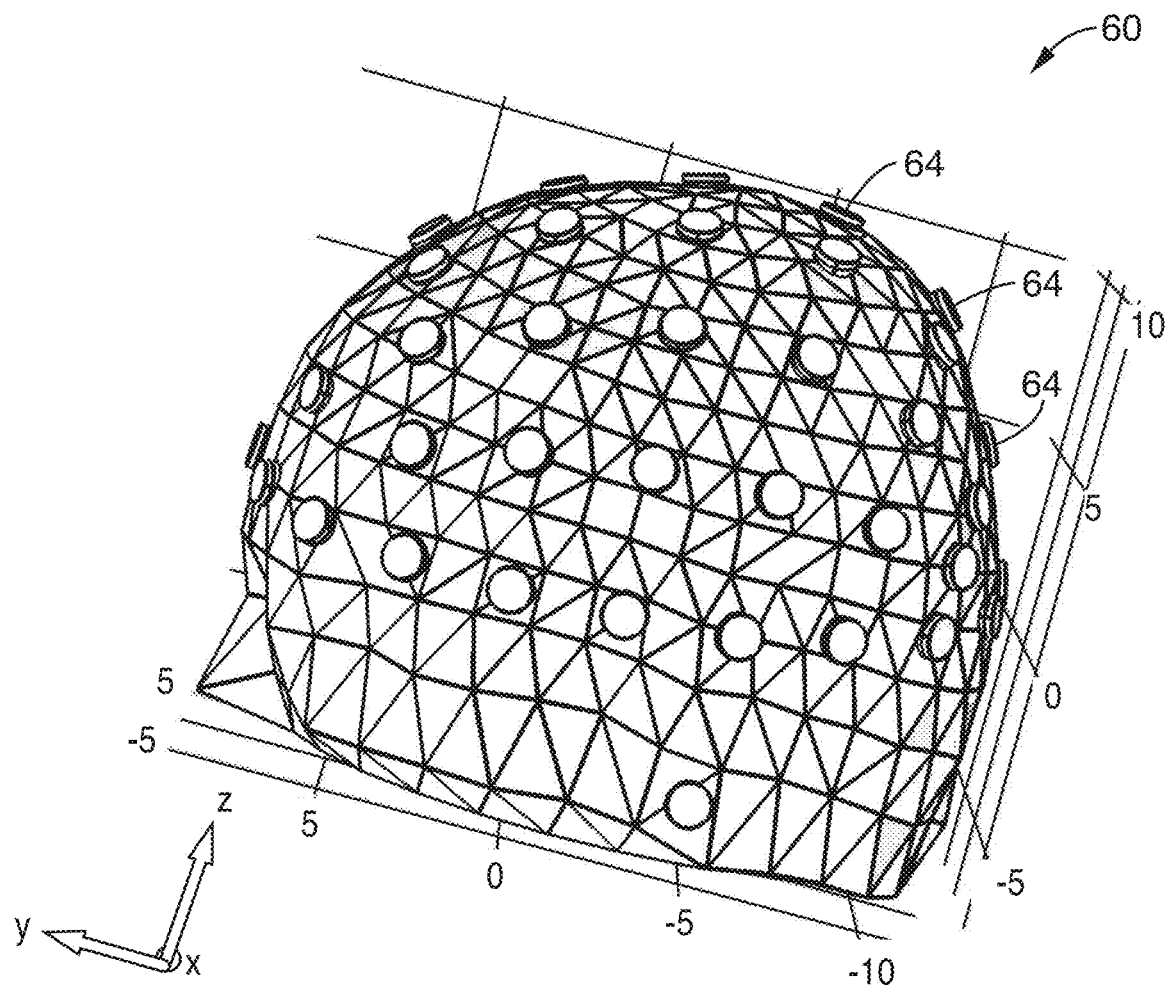

FIG. 8 shows a 3D head model with electrodes and course mesh pattern.

Figure 9:
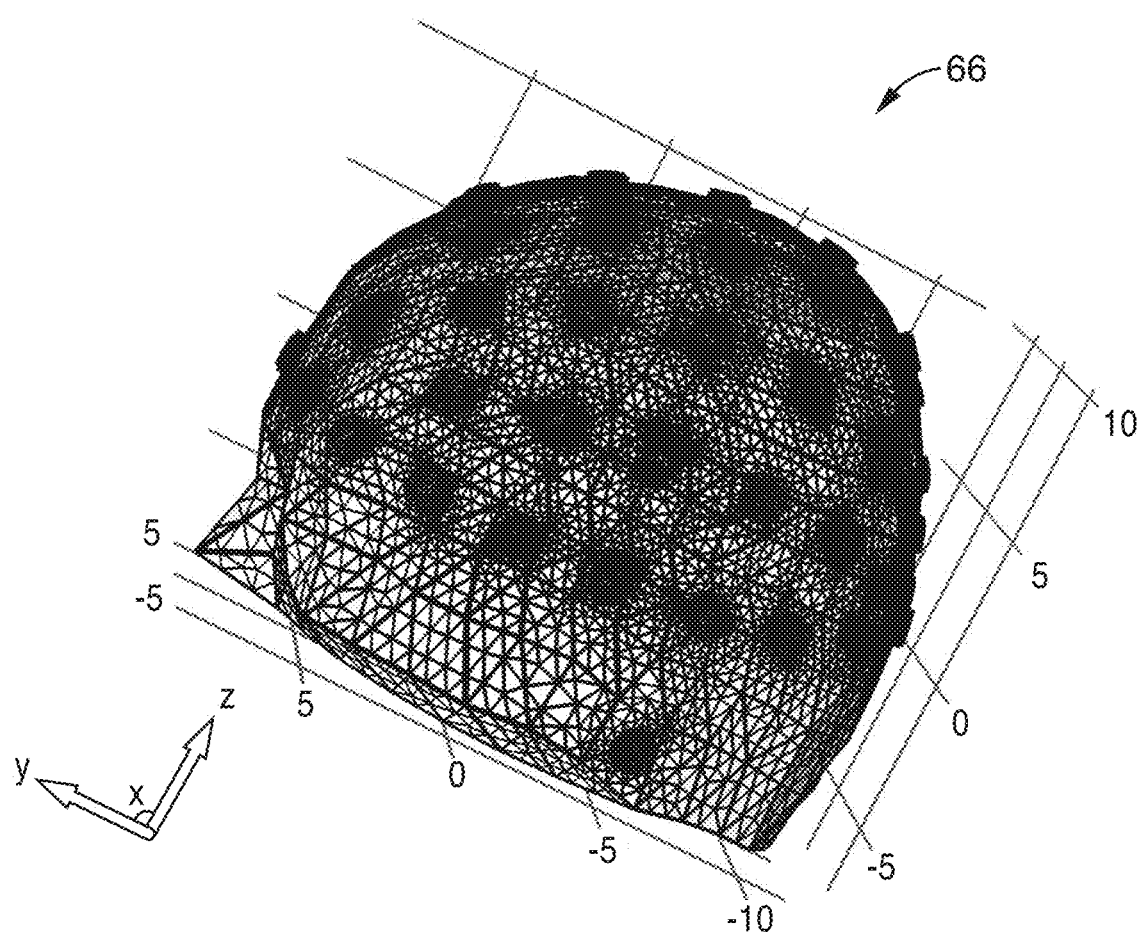

FIG. 9 shows a 3D head model after meshing is applied.

Figure 10A:
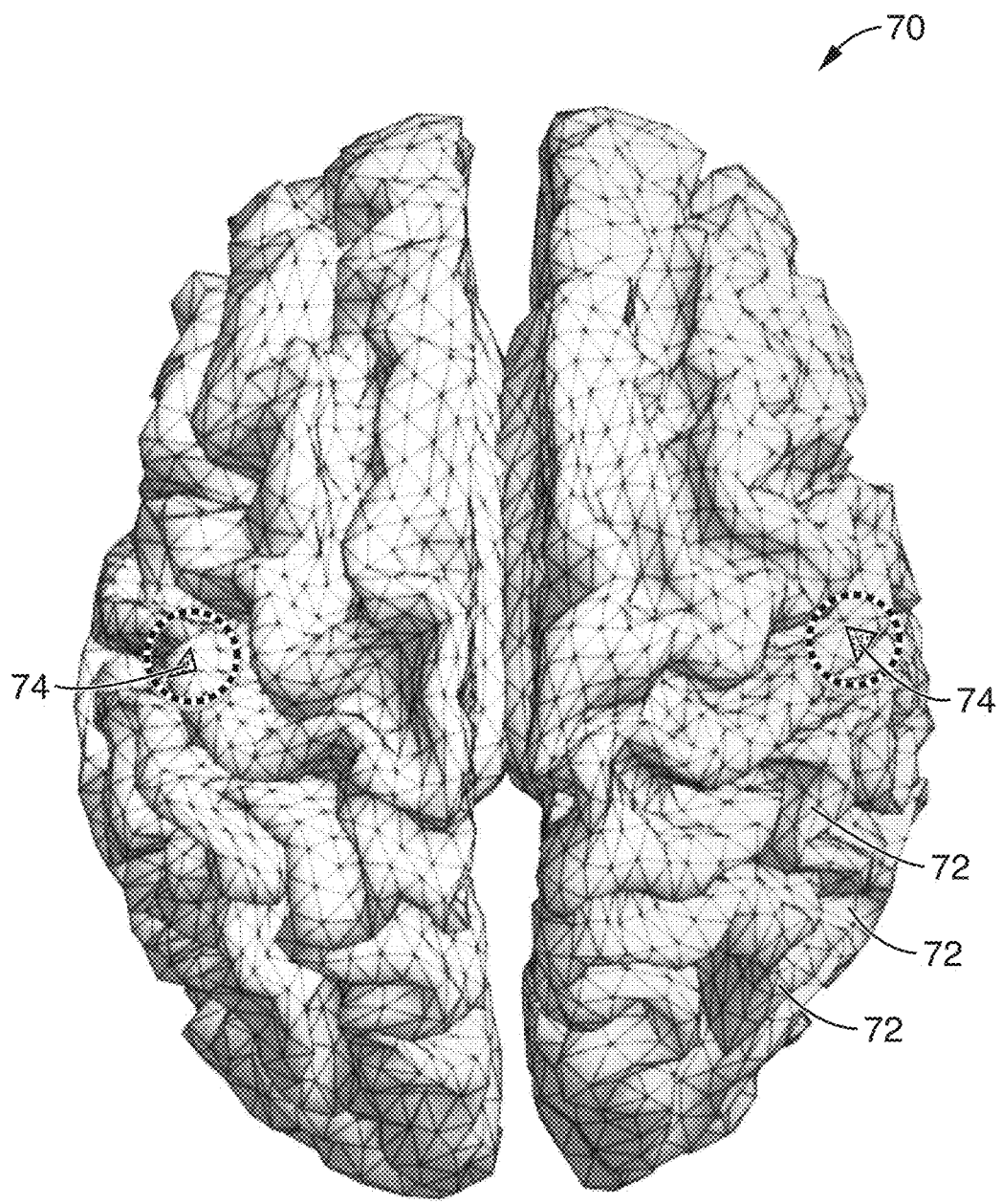

FIG. 10A shows a top view of a 3D brain model with mesh pattern and the target locations.

Figure 10B:
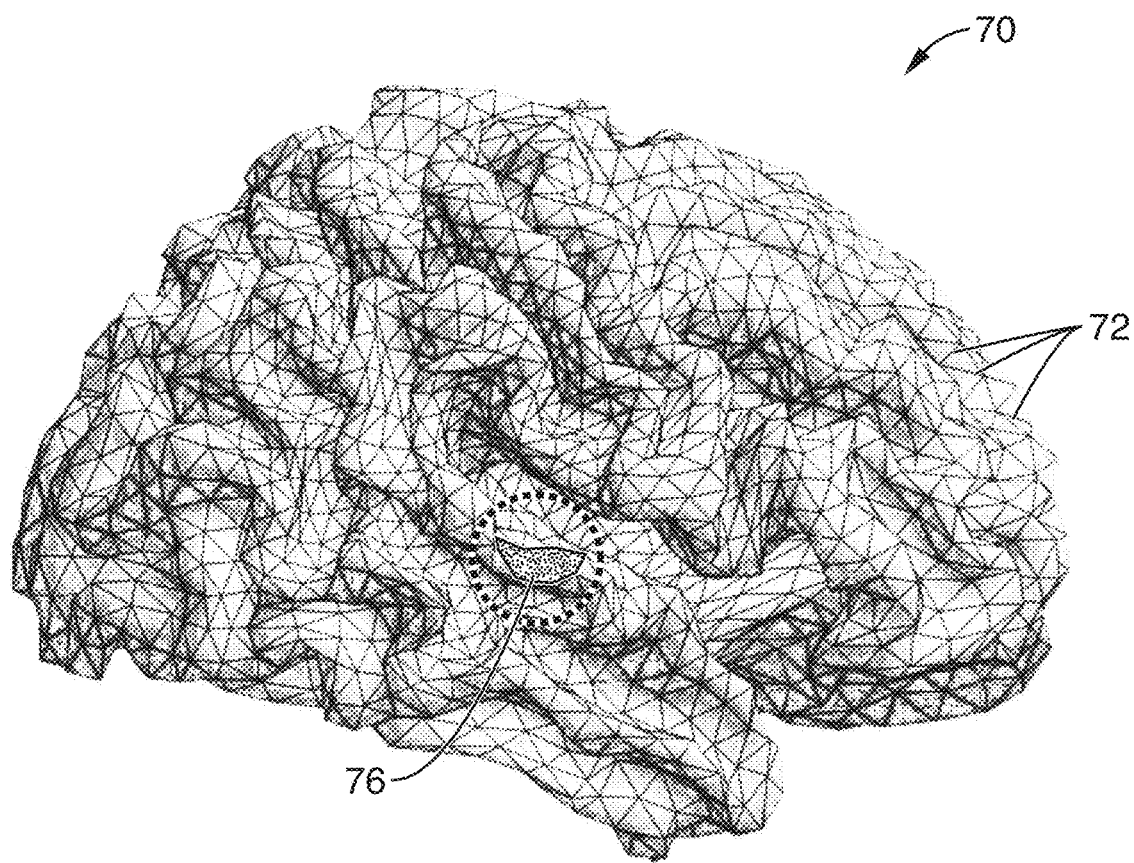

FIG. 10B shows a side view of the 3D brain model with avoidance region.

Figure 11A:
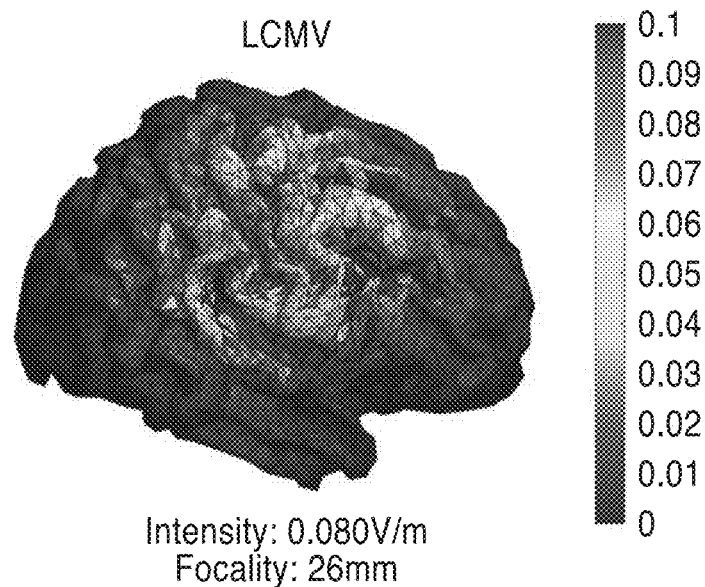

FIG. 11A shows the resulting electrical field for the LCMV method.

Figure 11B:
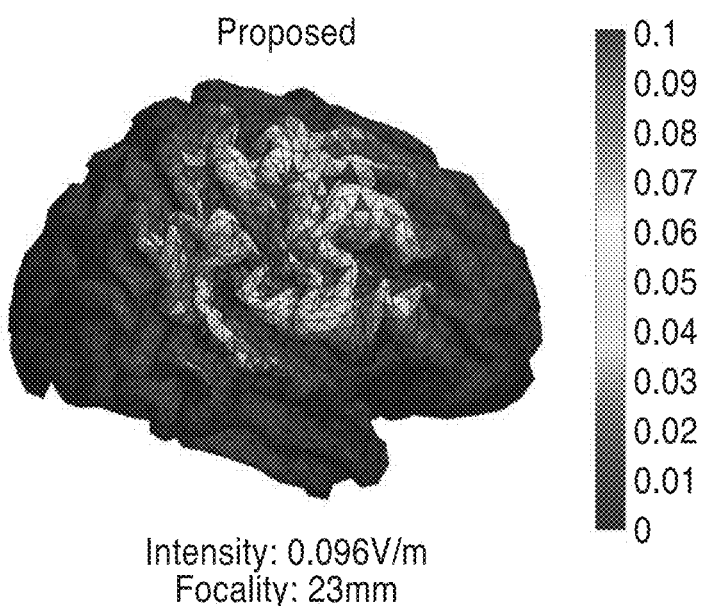

FIG. 11B shows the resulting electrical field for the optimization method of the present description.

Figure 12A:
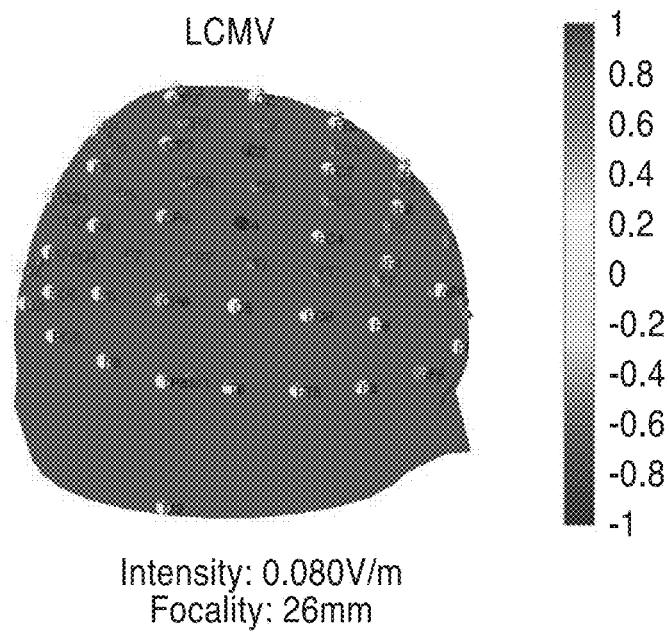

FIG. 12A shows the weighting for each electrode used for the LCMV method.

Figure 12B:
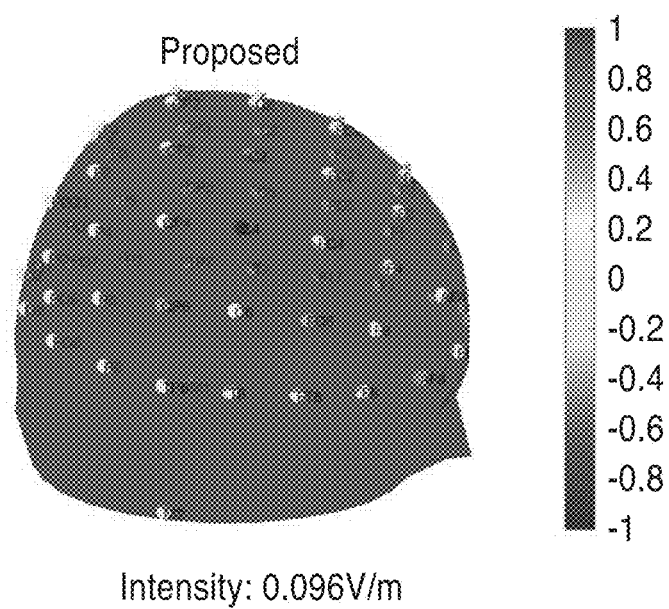

FIG. 12B shows the weighting for each electrode used for the optimization method of the present description.

Figure 13:
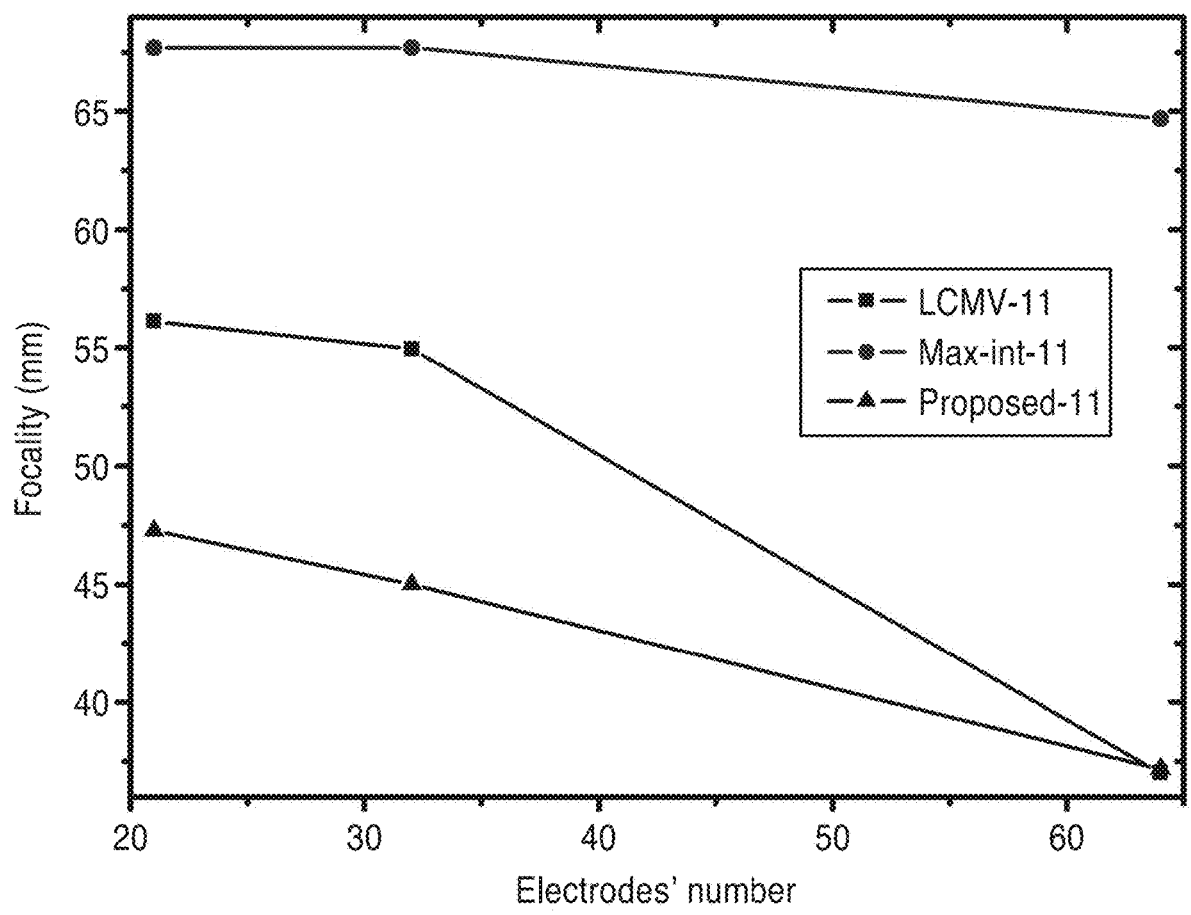

FIG. 13 shows a plot of the focality of the LCMV method, maximum intensity method and the optimization method of the present description with varying electrode number.

Figure 14:
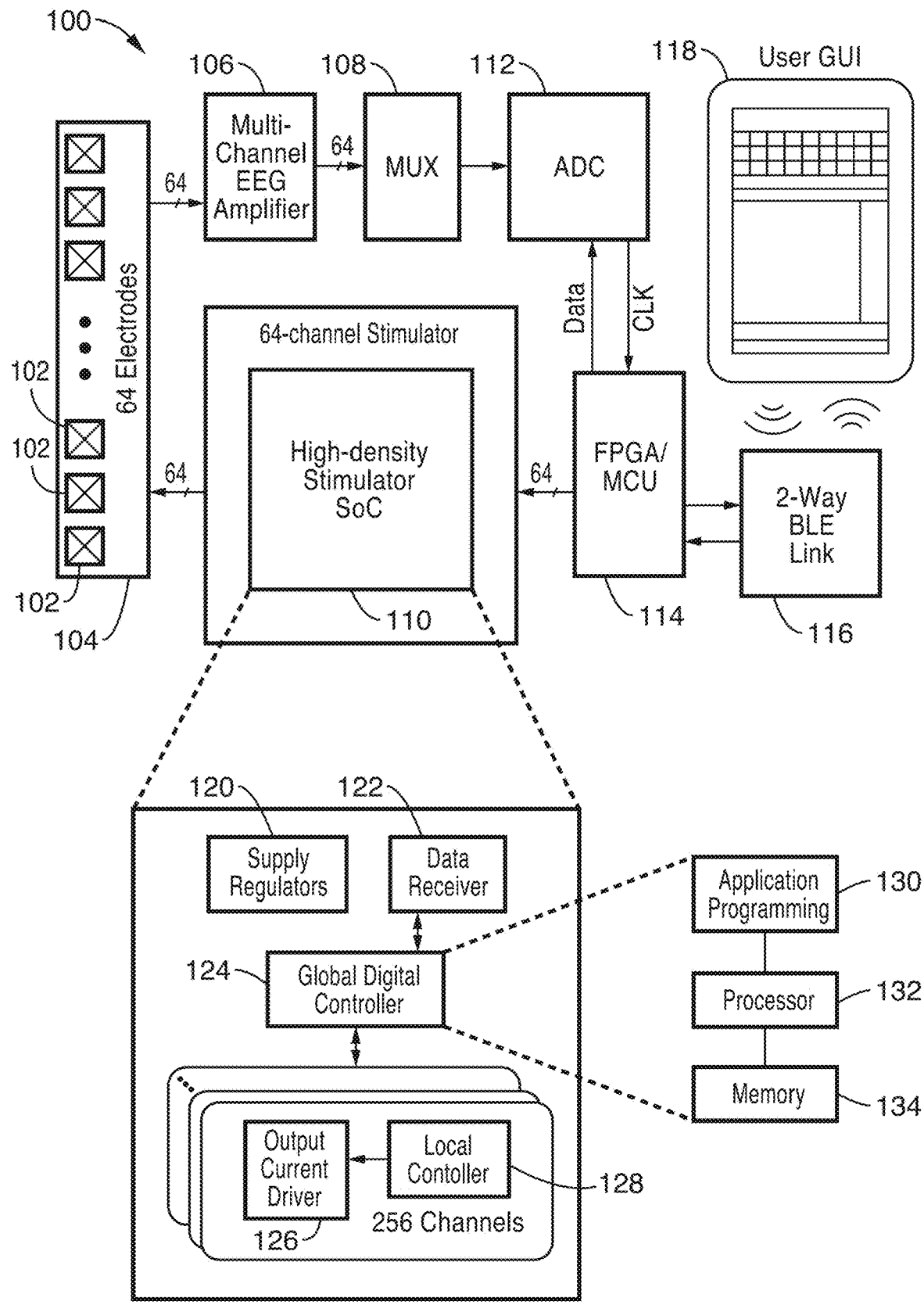

FIG. 14 shows a schematic diagram of a stimulation system with multi-channel stimulation SoC in accordance with the present description.

Figure 15:
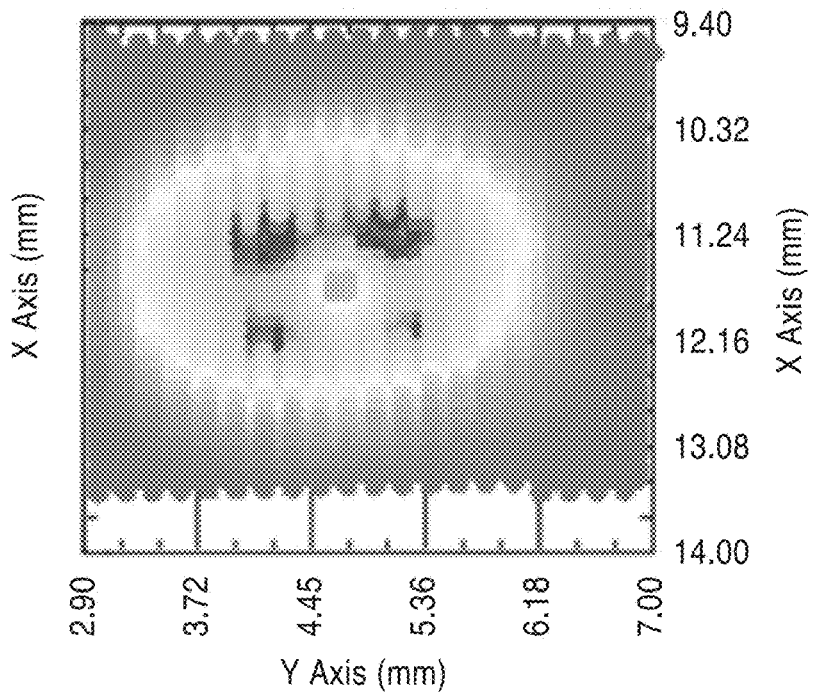

FIG. 15 shows an image of E-field from in-vitro stimulation using simultaneous multi-channel stimulation.

Figure 16:
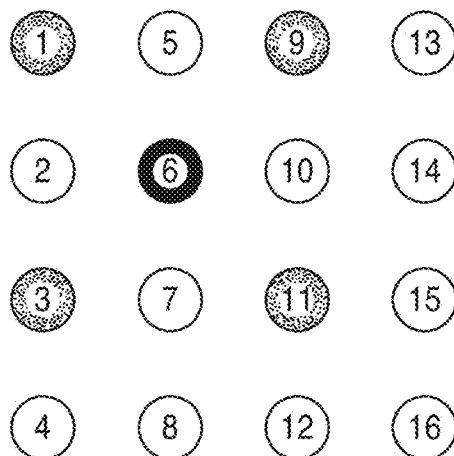

FIG. 16 shows a diagram of an electrode array using five electrodes for multi-channel stimulation.

Figure 17:
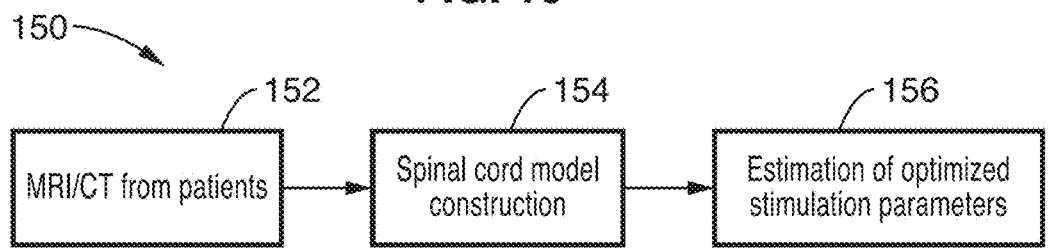

FIG. 17 shows a flow diagram for construction of a spinal cord 3D model.

Figure 18:
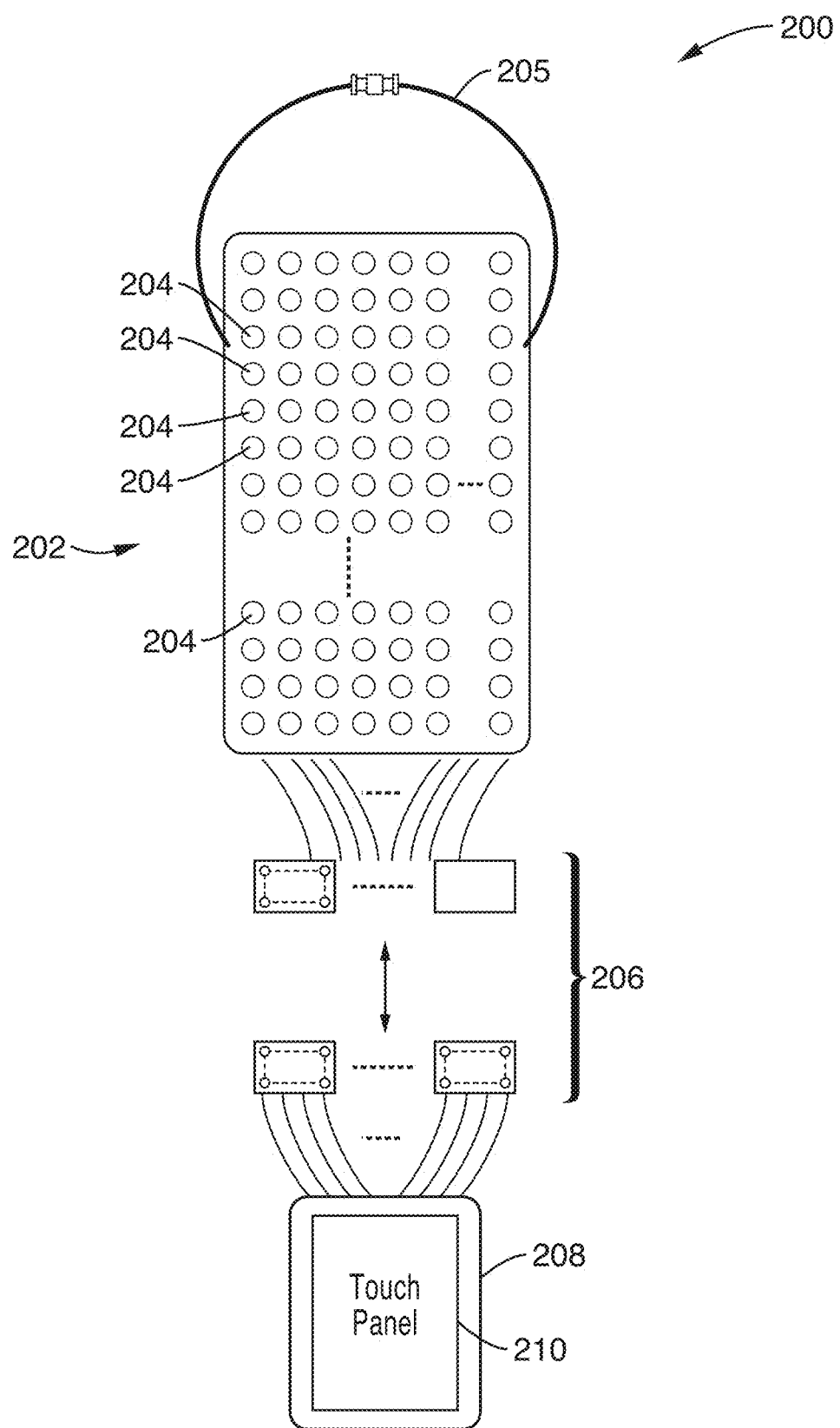

FIG. 18 shows a schematic diagram of a transcutaneous multi-electrode array and stimulator in accordance with the present description.

Figure 19:
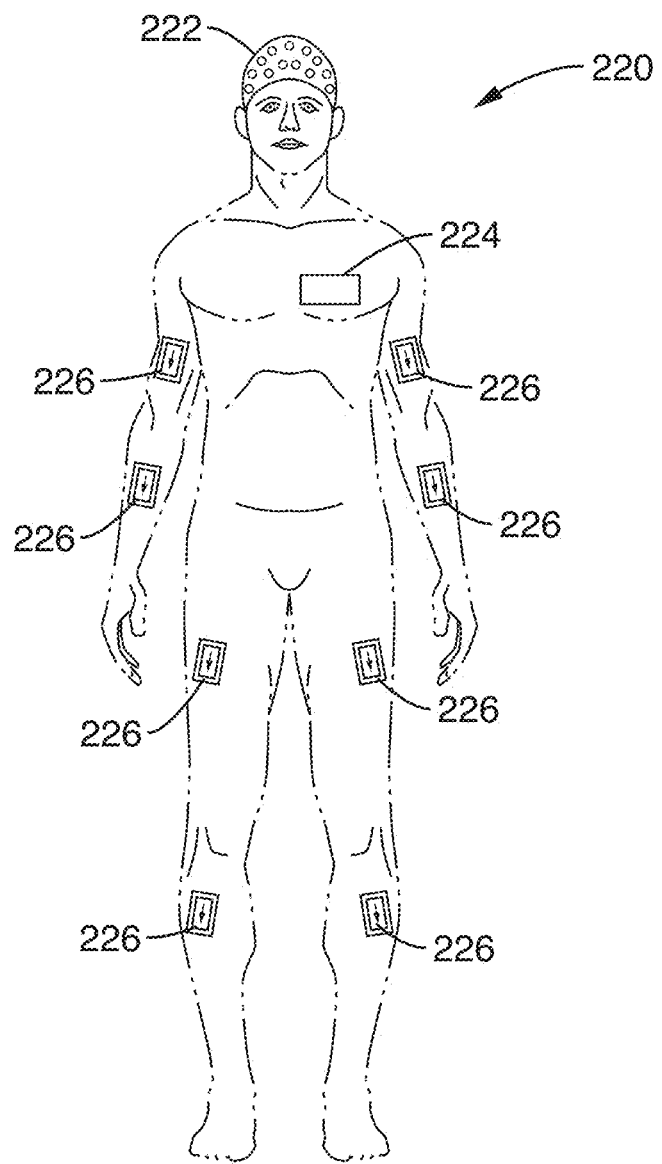

FIG. 19 shows a schematic diagram of a therapeutic spinal cord stimulation system positioned on a patient.

Figure 20:
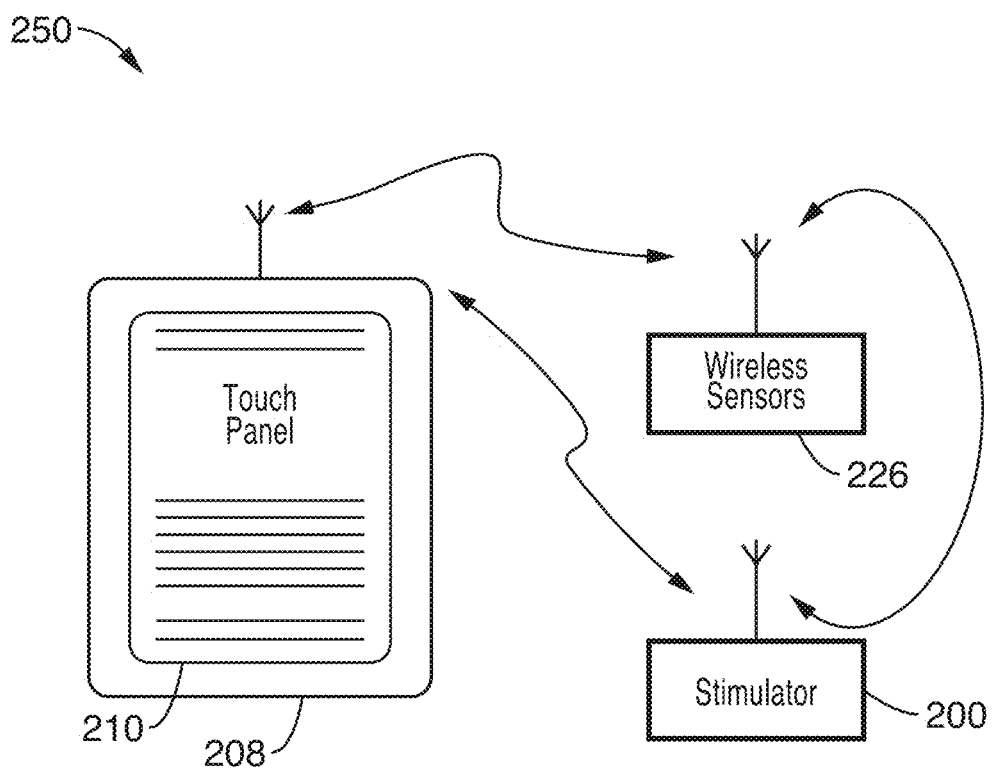

FIG. 20 is a schematic block diagram of a wireless sensing and stimulation system with a controller configured to be held by the patient or the clinician.

Figure 21:
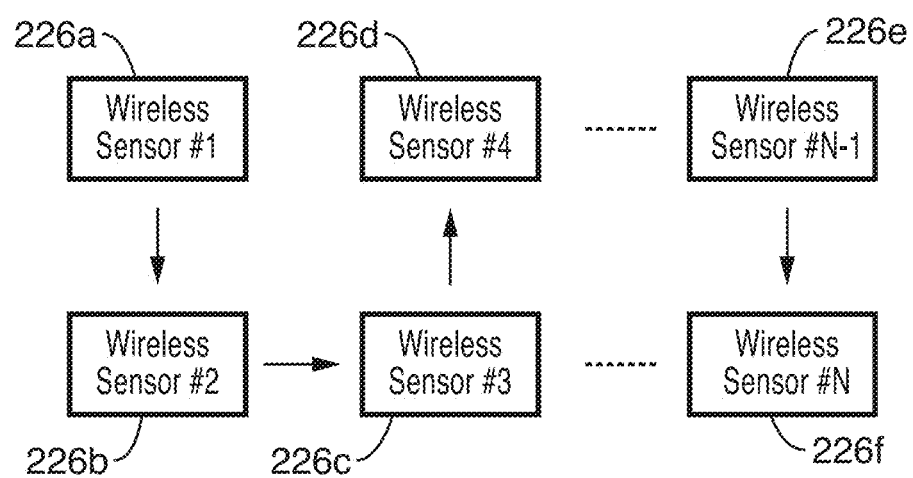

FIG. 21 is a schematic block diagram of a sensor network in accordance with the present description.

Figure 22:
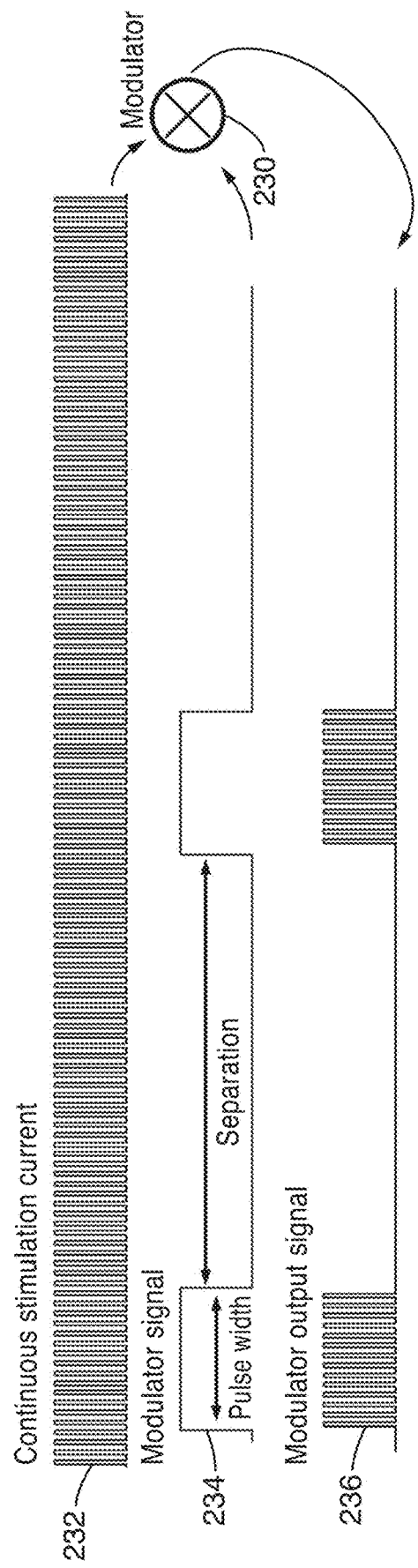

FIG. 22 shows a diagram for an exemplary modulator and modulator output for the system and methods of the present description.

DETAILED DESCRIPTION

The key challenges for noninvasive transcutaneous spinal cord stimulation and transcranial current stimulation lie in the ability to provide high spatial and temporal resolution, with a high degree of focal accuracy, while using the correct intensity and directionality using external current injection though an electrode on the skin.

To accommodate the above mentioned challenges, a multi-electrode system is described below. The multi-electrode system of the present technology includes novel hardware, software, algorithms, and user interface that enable an experiment methodology and development of clinical protocols by (1) a computational 3D model based on MRI/CT data to facilitate the treatment, efficacy, and safety of the device; (2) a novel source localization algorithm to obtain precise target localization and focal precision; (3) optimal stimulation patterns with desired intensity guided by a novel source localization algorithm; (4) miniaturized and fully integrated hardware electronics to independently drive each of the multi-electrodes, and thus offering the portability and flexibility at of a lower cost system; and (5) a sophisticated but user-friendly graphical user interface that will enable home use.

The system and methods of the present description are able to achieve focal and precise stimulation for transcutaneous spinal cord stimulation, and can be used to target single or multiple sites, as well as avoid certain regions. It is also capable of targeting any location with any orientation depending on different applications. Optimization techniques are combined with precise spinal cord modeling to provide optimal stimulation parameters for transcutaneous spinal cord stimulation. The system and methods of the present description makes full use of each electrode in a multi-electrode array to achieve focal and precise stimulation. It has also been demonstrated that the methodology of the system and methods of the present description can be equivalently applicable to transcranial current stimulation, and possibly the noninvasive internal organ stimulation.

To overcome the limitations of existing systems, the system and methods of the present description employ a novel optimization technique that provides a solution with both high intensity and high focal accuracy within the safety constraints. In particular, for the spatially extended target, the algorithm of the system and methods of the present description is able to provide various current intensity distribution (e.g., uniform, smooth, Gaussian, etc.) at the target depending on the application.

Another limitation of previously disclosed optimization methods is that they require the clinician to specify location and intensity of the target, which is usually unknown in most applications. With use of dynamic EEG brain imaging disclosed in PCT International Application No. PCT/US2016/050452 filed on Sep. 6, 2016 and published as WO 2017/044433 A1 on Mar. 16, 2017, and precise EEG source localization, the systems and methods of the present description is able to provide the accurate information of the target location, number as well as orientation, so as to enable a precise stimulation.

The EEG brain imaging system of the present description is able to provide much higher temporal resolution in the range of milliseconds rather than seconds. In addition to guide dynamic stimulation of the neural networks, the concurrent EEG brain imaging will also offer real-time feedback of the neuromodulation. Thus, a closed-loop stimulation is contemplated. Similarly, for transcutaneous spinal cord stimulation, EMG inverse imaging reconstructed from the electrical potential recorded by the surface electrodes may be used as a guidance.

1. Mathematical Formulation and Modeling of Spinal Cord Model

Figure 1:
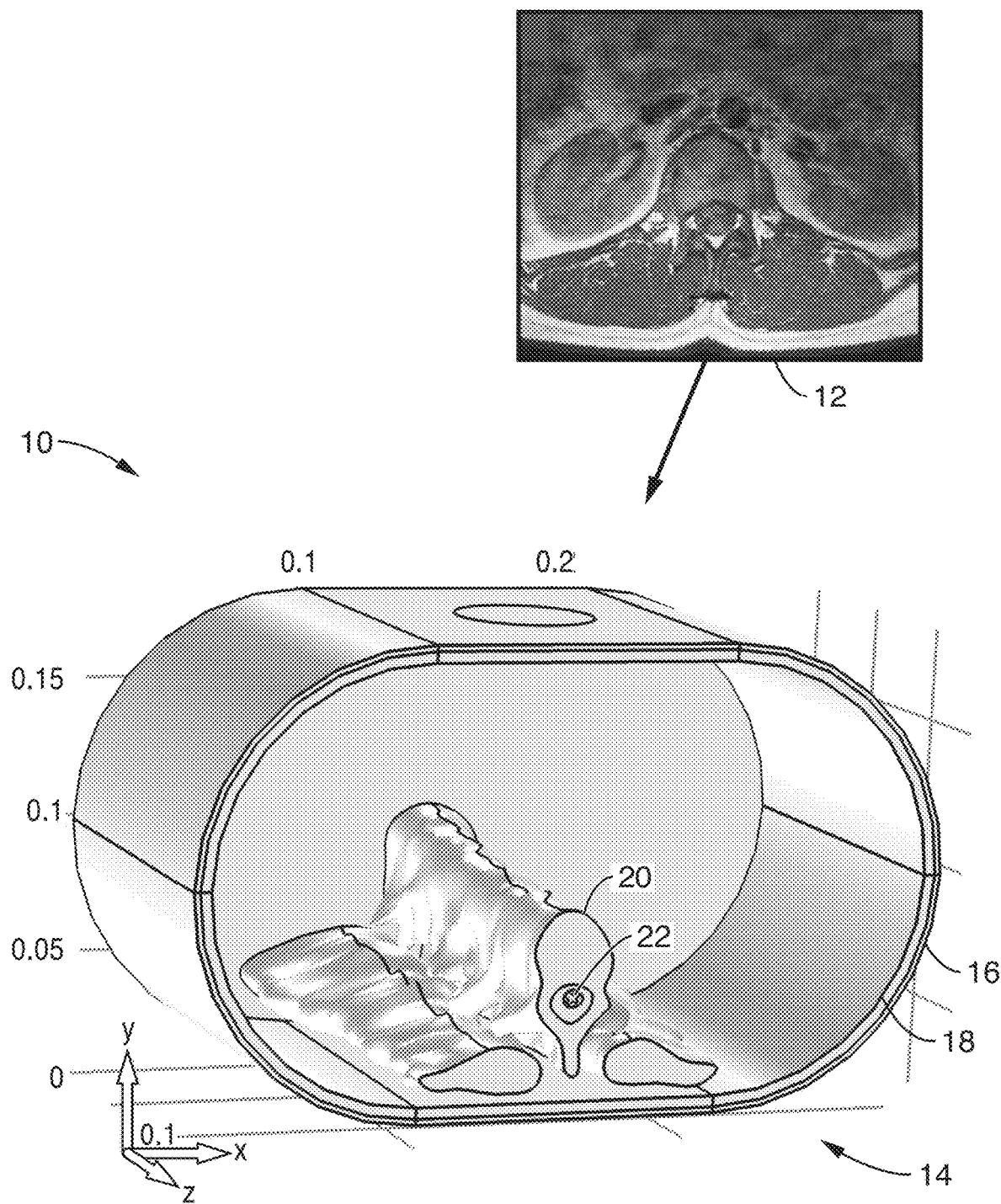
FIG. 1 shows a perspective view of a 3D spinal cord model generated from an individual MRI/CT image in accordance with the present description.

FIG. 1 shows an image of a computer generated spine model 10 generated from a CT/MRI image 12. A spinal cord model with different tissues is assumed, with each tissue having isotropic conductivity. Assuming N electrodes on the skin of the back, and one large return electrode on the belly.

We use a vector $x \in \mathbb{R}^{N*1}$ to represent the injected current at each electrode. Further, we discretize the whole spinal cord volume into M voxels, and use vector $e \in \mathbb{R}^{3M*1}$ to represents the electrical field of each voxel resulting from the electrical stimulation. Since we further consider the orientation of the electrical field, so the vector e has a dimension of 3M*1. Under quasi-static condition, the electrical field e in the voxels and the stimulation parameters x at the electrodes has a linear relationship:

$$e = Kx. \qquad \text{Eq. 1}$$

Here the coefficient matrix K is called "lead field matrix", which describes the one to one mapping between each electrode and each voxel. Specifically, the $(i,j)^{th}$ entry of K denotes the electrical field at the $i^{th}$ voxel due to an unit current stimulation at the $j^{th}$ electrode. Therefore, the electrical field in each voxel is a linear superposition of that resulting from the injected current from each electrode. The K matrix can be calculated by constructing a spinal cord model and solving the Maxwell's equations with the boundary element method (BEM) or finite element method (FEM).

To calculate the lead field matrix, a spinal cord model is first constructed. A 3D spinal cord model is generated based on a high-resolution CT/MRI image, which includes the following steps: image segmentation, electrode model construction, meshing. The FEM method to calculate the lead field matrix in Eq. 1.

(a) Image Segmentation

Referring to FIG. 1, the torso 14 of model 10 is segmented into different tissues according to the gray level on the MRI/CT image 12. The segmentation can be done manually in software such as Solidworks, or automatically in software such as MeVisLab. For tissues that are difficult to be identified from the image 12, portions of the model may be built manually using software such as Solidworks, COMSOL, or the like.

After image segmentation, 2D segmentation results are converted into a 3D tissue model for each tissue, e.g., using Solidworks or like software. All of the tissue are then assembled together to form a whole 3D model 10 as shown in FIG. 1. FIG. 1 shows a 3D model 10 with different tissues, such as skin 16 (including stratum corneum (SC), stratum germinativum (SG) and dermis layers), fat/muscle 18, vertebrae 20, spinal cord/nerve 22 (gray and white matters), cerebrospinal fluid (CSF), etc.

(b) Electrode Model Construction

Figure 2:
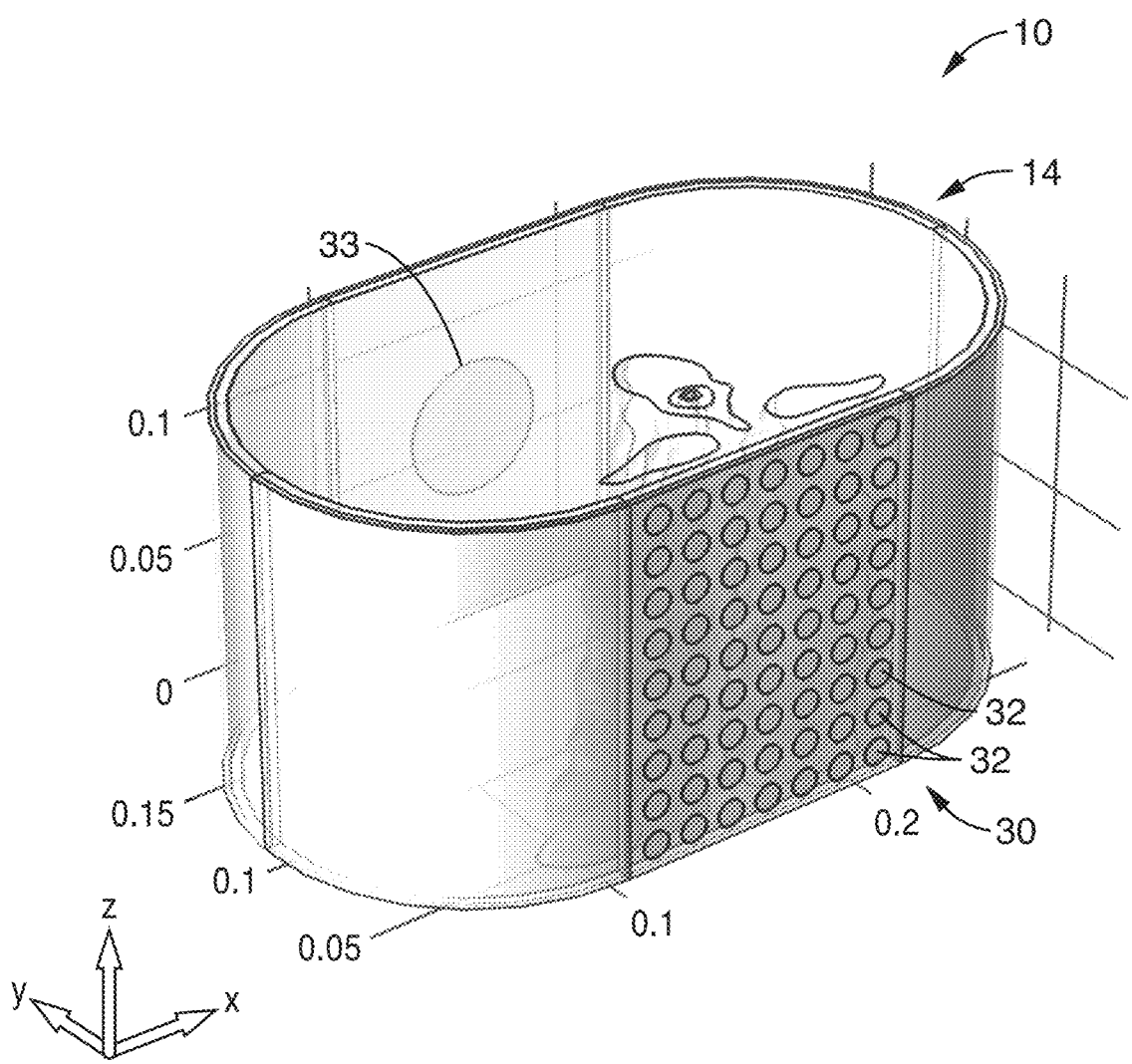
FIG. 2 shows a perspective view of the spinal cord model of FIG. 1. integrated with a multi-electrode stimulation array.

Referring to FIG. 2, after constructing the 3D tissue model 10 for the spinal cord, we import the model into software such as COMSOL, and construct an electrode model 30. The electrode model 30 includes a multi-electrode array of electrodes 32 on the back and one return electrode 33 on the belly. FIG. 2 shows an array 30 of 9 (rows)*7 (columns) of small electrodes 32 for stimulation and one large electrode as the return 33. In one exemplary model, the electrodes 32 are composed of a stainless steel material with thickness of 60 μm and diameter 1 cm. It is appreciated that other electrode array configurations, as well as electrode composition/dimension, may be contemplated. The electrode material, size, pitch, thickness, position, etc. may be modified as appropriate in the modeling software.

(c) Meshing

Figure 3:
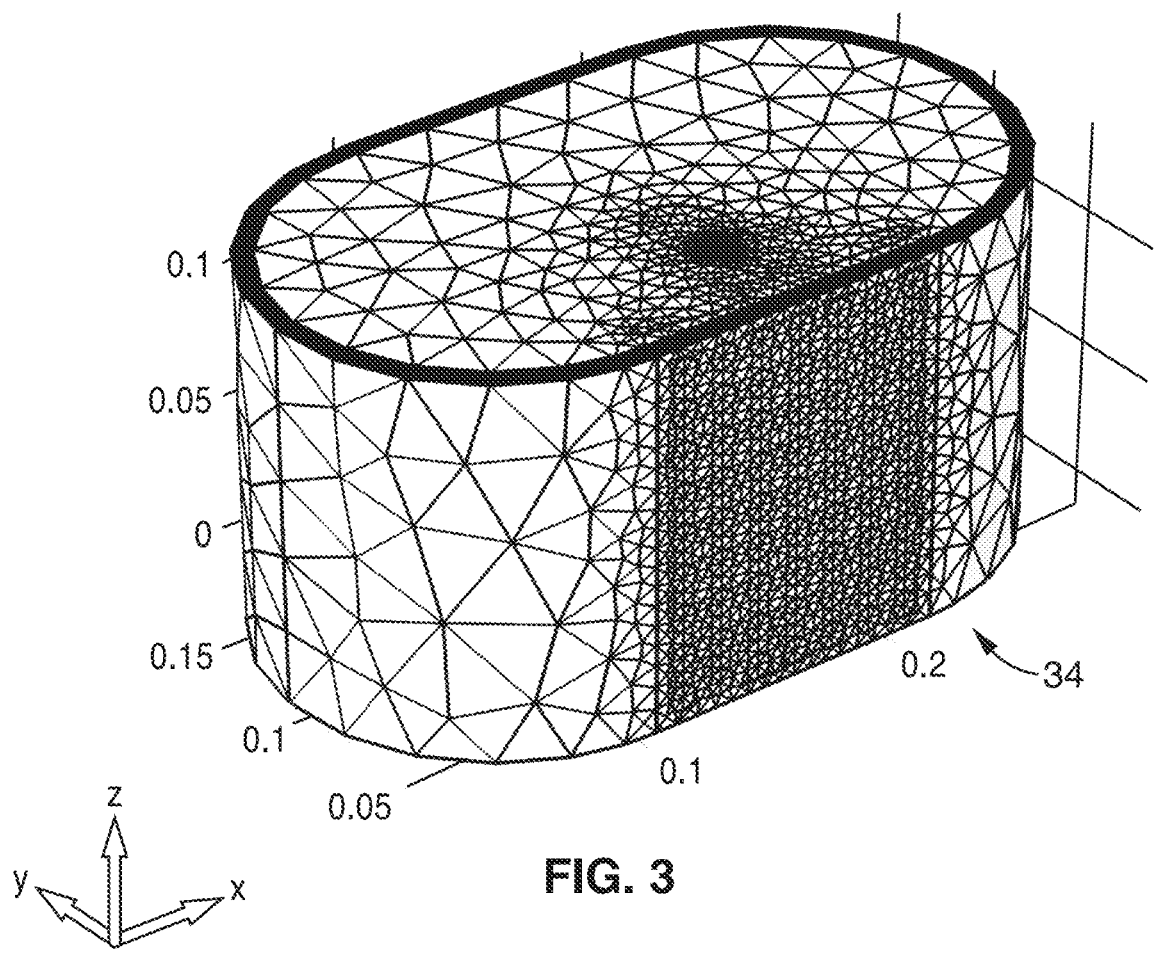
FIG. 3 shows a perspective view of the spinal cord model of FIG. 1 after meshing.

Referring to FIG. 3, the whole model (which includes the tissue model 10 and electrode model 30) is then discretized into a large number of voxels to form a finite element model 34.

(d) Lead Field Matrix Calculation

To calculate the lead field matrix of Eq. 1, any finite element method software, such as COMSOL, may be implemented. For each electrode 32, a unit current (density) assigned, and the resulting voltage/E-field/current (density)/activation function is calculated at each voxel. The obtained values form a vector, which will become the corresponding column for the lead field matrix. Repeating this process will result in the whole lead field matrix. Table 1 lists the conductivity values for different tissues used to calculate the lead field matrix.

2. Optimization Methods

This section details a novel method to design and configure optimal stimulation parameters for transcutaneous spinal cord stimulation (tSCS) to improve the focal accuracy of tSCS. This method overcomes the limitation of maximum intensity and LCMV methods, and is able to obtain both high intensity and focality at the target.

(a) Safety Limit

First, the safety limit of transcutaneous spinal cord stimulation is determined. With a carrier frequency of 10 kHz, the subject can easily tolerate a stimulation intensity from 30 mA to 200 mA and not feel pain. Therefore, a reasonable safety criteria assumes a current intensity for each electrode that is limited to 100 mA, with the total current intensity limited to 200 mA, and the intensity in the avoidance region is at least 10 times smaller than that in the target region. Using $I_{max}$ to represent the maximum current at each electrode, $I_{total}$ to denote the maximum total current injected to the body, and ratio to represent the intensity ratio between the target and avoidance region, the safety criteria are summarized according to FIG. 2 through FIG. 5:

$$\begin{cases} |x_i| \leq I_{max}, \, i = 1, \ldots, N & \text{Eq. 2} \\ \sum_{i=1}^{N} |x_i| \leq 2*I_{total} & \text{Eq. 3} \\ \sum_{i=1}^{N} x_i = 0 & \text{Eq. 4} \\ Intensity_{avoid} \leq \frac{1}{ratio} Intensity_{target} & \text{Eq. 5} \end{cases}$$

Note that since the total positive current is equal to the total negative current (Eq. 4), therefore the sum of absolute value of the current should be twice of the total current injected to the body (Eq. 3). It is worth noting that the suggested safety limit values $I_{max}$=100 mA and $I_{total}$=200 mA can be easily modified for different applications.

(b) Optimization Model

The key challenges for noninvasive stimulation technologies lie in the capability of providing precise stimulation with both high focal accuracy and intensity in the desired direction. Current optimization methods either maximize the intensity at the target by satisfying the focal accuracy (e.g., maximum intensity method), or maximize the focal accuracy at the expense of low intensity (e.g., Linear Constrained Minimum Variance (LCMV)). In addition, in the LCMV method and it variants, a hard constraint is enforced to meet the specified intensity and orientation at the target, which may lead to infeasible solution when the specified intensity is high or the target region is large. To overcome these limitations, the optimization method of the present description always provides a feasible solution that includes both high intensity and focal accuracy within the safety constraints. This model can be expressed as follows:

$$x_{proposed} = \arg\min_{x} \frac{1}{w}\|Kx\|_2^2 - \lambda * e_0^T Cx \quad \text{Eq. 6}$$

$$\text{subject to} \begin{cases} |x_i| \leq I_{max}, \, i = 1, \ldots, N \\ \sum_{i=1}^{N} |x_i| \leq 2*I_{total} \\ \sum_{i=1}^{N} x_i = 0 \\ Intensity_{avoid} \leq \frac{1}{ratio} Intensity_{target} \end{cases}$$

where the constant w is equal to the ratio between the total number of voxels and the number of targeted voxels. The first term is the focality term, the second term is the intensity on the desired direction. The parameter λ balances these two objectives and controls the relative importance of the focality and directional intensity, e.g., by applying a weighting to the focality and directional intensity terms. It can be set empirically or automatically by the L-curve method or cross validation method. This optimization problem is convex, which can be solved by software such as CVX efficiently.

The algorithm detailed in Eq. 6 is able to deal with any target location on any tissue (e.g., bone, white matter) with any target orientation. It can not only deal with multiple targets, but also avoid activating certain sensitive regions. In addition, it is very easy to incorporate various safety constraints into the model. Rather than setting a hard constraint at the target like the LCMV method, it allows a range of the intensity by changing the parameter λ. It optimizes intensity and focality simultaneously.

To further improve the focality, we can replace the L2 norm with L1 norm to impose sparsity on the stimulated area, as follows $$x_{proposed} = \arg\min_{x} \frac{1}{w}\|Kx\|_1 - \lambda * e_0^T Cx \quad \text{Eq. 7}$$

Furthermore, for the spatially extended target, the algorithm is able to provide various current intensity distribution (e.g., uniform, smooth, Gaussian, etc.) at the target depending on the applications. This can be achieved by imposing sparsity on a transform domain, rather than the original domain:

$$x_{proposed} = \arg\min_{x} \frac{1}{w}\|D(Kx)\|_1 - \lambda * e_0^T Cx \quad \text{Eq. 8}$$

where the operator D is the total variation operator (first order difference operator) if uniform distribution is desired; or Laplacian operator if smooth distribution is desired. If highly smooth/Gaussian distribution is desired, total generalized variation (TGV) may be used for the second term.

(c) EEG/EMG Inverse Image Guided Optimal Stimulation

One of the limitations of conventional optimization methods is that they require the clinician to specify the location and intensity of the target area, which is unknown in most applications.

Different from the reciprocity principle-based methods that use an EEG signal as a guide, the system of the present description may be configured to use a dynamic EEG brain image system (as described in UC16-151-2FP, incorporated herein by reference in its entirety) as a guide for electrical stimulation. Compared to fMRI, EEG brain imaging provides much higher temporal resolution (~ms). It is able to provide not only the number, the location but also the orientation of targets. With precise EEG source localization, the system is able to provide the ability to deal with complicated target/avoidance configurations, and with spatial high accuracy. The concurrent EEG brain imaging not only provides a guide for dynamic stimulation of complicated neural networks, but also offers real-time feedback of the neuromodulation. Thus, a closed-loop stimulation is eminently possible.

Similarly, for transcutaneous spinal cord stimulation, the surface multi-electrode array may be used to record the electrical signal, and calculate the solution of the inverse problem to find out the targets, then use the targets as a guidance for the optimization solver.

(d) Simulation Protocol

Figure 4A:
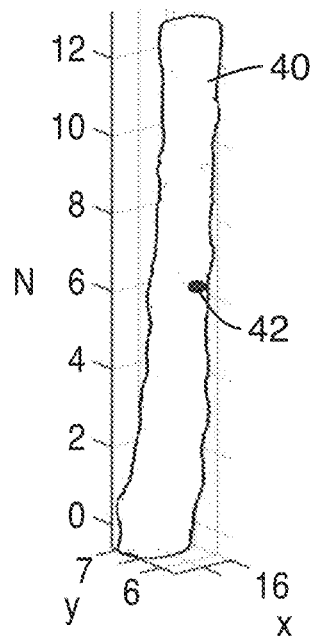
FIG. 4A shows an image of a spinal column with a single simulated target.
Figure 4B:
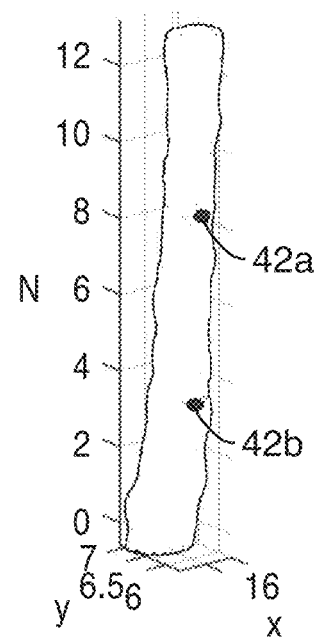
FIG. 4B shows an image of a spinal column with a multiple simulated targets.
Figure 4C:
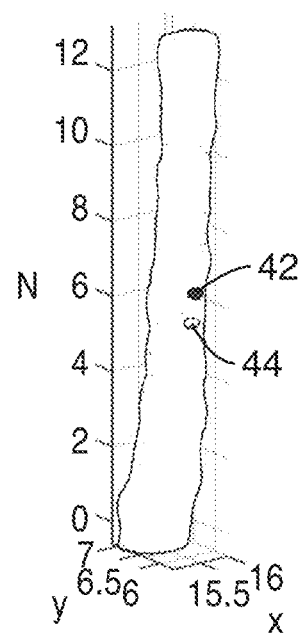
FIG. 4C shows an image of a spinal column with a single simulated target one nearby avoidance region.

Referring to FIG. 4A to FIG. 4C, a study was performed by simulating three different target configurations to test the performance of our method in different cases, including 1) single target case (FIG. 4A), in which there is only one target region 42; 2) multiple targets case (FIG. 4B), in which there are two target regions 42a and 42b; and 3) avoidance case (FIG. 4C), in which one target 42 is stimulated along with a nearby avoidance region 44. For the transcutaneous spinal cord stimulation, the default target tissue is white matter. This is because in many applications, such as locomotor behavior regulation and pain control, the target region is dorsal root or dorsal column. Except for white matter, the case of the target location on the vertebra was also tested (e.g., a spot on the vertebra where there is a cavity was chosen so that the current can flow in to spinal cord). The results were compared with that of white matter. For the target orientation, the default orientation is along y-axis (radial to the electrode), but the orientation of z-axis was also tested, and a comparison between them was made.

(e) Quantitative Metrics

In order to evaluate the performance of various methods quantitatively, we use the following criteria:

(i) Intensity (unit: V/m), defined as the average intensity at the target voxel;

(ii) Target Error (TE, unit: cm or mm), defined as the distance between center of mass of the activation area and the target; and (iii) Focality (unit: cm or mm), defined as the radius within which the accumulative energy (square of intensity) is half of the total energy.

Considering that the target orientation also plays an important role on the stimulation effectiveness, the following directional criteria are further adopted:

(i) Directional Intensity (DI, unit: V/m), defined as the average intensity in the desired direction;

(ii) Directional target error (DTE), which is similar to target error (TE). except for using directional intensity instead of total intensity when calculating TE; and (iii) Directional focality (DF, unit: cm or mm), which is similar to focality except for using directional intensity rather than total intensity.

In one embodiment, spinal cord stimulation parameters may comprise a current intensity from each electrode ranges from 0.01 mA to 250 mA, pulse width ranges from tens of μs tens of ms, and the time separation between stimulus or a group of stimuli ranges from 10 s to 0.001 s. The overall transient current intensity from all electrode is less than 250 mA.

3. Spin Model Results

In this section, the qualitative and quantitative results of various methods for transcutaneous spinal cord stimulation are shown. In order to make a fair comparison among different methods, the same safety criteria (Eq. 2-Eq. 5) was applied for all of the methods.

The method of the present description was compared with several existing methods in the literature: single large electrode, single small electrode, maximum intensity, ring configuration, and LCMV. FIG. 5A through FIG. 5C shows the stimulation results for the method of the present description, with FIG. 5A showing the electrode weighting, FIG. 5B showing the intensity E-field, and FIG. 5C showing the Directional E-Field.

For single large electrode, single small electrode, and the maximum intensity methods, the intensity of E-field at the target is very high. However, the E-field is spread out, resulting in very low focal accuracy. Among all the methods, the maximum intensity method provides the highest directional intensity and the worst focality. In comparison, the results of ring configuration, LCMV and optimization method of the present description are much more focal. Compared to the other two methods, the optimization method of the present description provides the best results in terms of both intensity and focality.

The optimization method of the present description is able to target any location including any tissue such as bone and white matter. Deeper source is generally more difficult to target, in terms of intensity and focality. For example, the results of targeting bone vs. targeting white matter were also compared. Results show that targeting bone provides much higher target intensity and focality accuracy than targeting white matter, which is reasonable since when targeting the white matter, the electrical field is weakened by the high-resistivity bone.

Except for target locations, optimization method of the present description is also able to target any orientation. FIG. 5A through FIG. 5C show results we set the target orientation to be along the y-axis (radial to the electrode). FIG. 6A through FIG. 6C, the results of target orientation along the z-axis (tangential to the electrode) are shown, and compare the performance of different stimulation methods. FIG. 6A shows the stimulation parameters for each method, and one can see that the weighting for each electrode is very different from that of y-axis orientation (FIG. 5A).

For target with z-axis orientation, generally the stimulation pattern is to place an anode on one side of z-axis and a cathode on the other side. The ring configuration has difficulty in dealing with tangential targets, which resulting in low target intensity and focality. To improve the focal accuracy, the LCMV method and the optimization method of the present description place multiple anodes with different weightings rather than only using single anode/cathode. Compared to other methods, the optimization method of the present description provides the best focal accuracy.

The optimization method of the present description is also able to deal with both single target and multiple targets. The optimization method of the present description provides better results than LCMV in terms of target intensity, localization accuracy, and focal accuracy. Compared to the results of single target, both target intensity and focality are lower in the multiple targets case, due to additional constraints on the solution.

With respect to avoidance regions, the ring pattern is unable to avoid certain regions. In contrast, optimization methods including the optimization method of the present description are able to achieve avoidance by constraining the intensity in the avoidance region to x times (e.g., x=10) lower than that in the target region. The performance of the LCMV method and the optimization method of the present description were compared in performance with dealing with an avoidance region close to the target region. The result shows that the LCMV avoids the region with the expense of shifting the activated area away from the target region, leading to larger target error and lower focality. The optimization method of the present description demonstrates much higher localization accuracy and focal accuracy than LCMV in this case.

The intensity and focality at the target have an inherent trade-off. In the optimization method of the present description, the parameter λ controls the relative importance between the target intensity and focality, and is critical to the stimulation results. When λ is large, more weight is put on the directional intensity term, therefore the intensity of the results will be high, and vise versa. By setting λ to be a very small value (e.g., 0.01), we can estimate the upper bound of the focality. On the other hand, when setting λ to be a very large value (e.g., 1000), we can obtain an upper bound of the intensity. As λ goes to infinity, the optimization method of the present description essentially becomes the maximum intensity method. To obtain a best result, selecting an appropriate value of λ is very important.

The LCMV method, the maximum intensity method and the optimization method of the present description were compared with different λ. The results show that as λ becomes larger, the directional focality decreases while the directional intensity increases. The result of λ=0.01 estimates the upper bound of directional focality, which is 0.59 cm, and that of λ=1000 estimates that of directional intensity, which is 27.3V/m. One can see that the results of λ=1000 matches with that of maximum intensity method. In addition, our method always obtains better results than LCMV in terms of focality and intensity. For example, when λ=2, our method provides a similar intensity to LCMV, but its focal accuracy is higher; when λ=4, it provides similar focality to LCMV, but the intensity is much higher.

By changing λ, we can estimate an upper bound of focality and intensity. When λ is very large, we get the best intensity; when λ is very small, we get the best focality. With an appropriate parameter λ, we can obtain an elegant solution with both high intensity and focality. The parameter λ can be selected manually by experience, or automatically using L-curve or cross validation methods.

Note that the above systems and methods may be applied not only to humans, but also to animals, e.g., rat, monkey, pig. In addition, it can be applied to any part of the spinal cord, including cervical, thoracic, lumbar, and sacral.

4. Brain Stimulation

In this section, the systems and methods detailed above were applied to transcranial current stimulation (tCS). We demonstrate that our method also outperforms other state-of-the-art methods in tCS. The procedures for extending to noninvasive internal organ stimulation are also described briefly.

(a) 3D Head Model

Using a similar method as the spinal cord model construction, a 3D head model and source model can be constructed from a high-resolution MR image. FIG. 7 shows a 3D head model built with various tissues: scalp 52, skull 54, CSF 56, and cortex 58.

In addition, an electrode model containing multiple electrodes was constructed, where the electrode locations were devised from the international standard 10-10 system. FIG. 8 shows a 3D head model 60 with 64 electrodes and course mesh pattern 62, and FIG. 9 shows a 3D head model 66 after meshing is applied. In the electrode models of FIG. 8 and FIG. 9, the electrodes use a gel material and 2 mm thick copper, with a diameter of 1.2 cm. Note that the electrode array and configuration may be varied by number, material, size, pitch, thickness and position can be easily modified.

With the generated 3D head model, FEM is used to calculate the lead field matrix in COMSOL. For the conductivity of each tissue, published values were used.

(b) Safety Limits for Transcranial Current Stimulation

For transcranial direct current stimulation (tDCS), there have been different proposed safety criteria, including limits for total current, current density, charge density, duration, etc. A common criteria shared by most literature is that the total current should be less than 2 mA. In the present study, both total current and current were restricted for individual electrodes. Specifically, the following constraints were used:

$$\begin{cases} |x_i| \leq I_{max}, i = 1, \ldots, N \\ \sum_{i=1}^{N} |x_i| \leq 2 * I_{total} \\ \sum_{i=1}^{N} x_i = 0 \\ Intensity_{avoid} \leq \frac{1}{ratio} Intensity_{target} \end{cases}$$

where the $I_{max}$ is set to be 1 mA, the $I_{total}$ is set to be 2 mA, and the intensity ratio between the target and avoidance region is set to be 10 in this study. Note that these values can be easily modified to satisfy the requirements of different applications.

To test the performance of the optimization method of the present description on transcranial current stimulation, several different cases were simulated, including: single targets, multiple targets and avoidance region on the cortex surface. FIG. 8 shows a 3D head model 60 with 64 electrodes and course mesh pattern 62, and FIG. 9 shows a 3D head model 66 after meshing is applied. FIG. 10A shows a top view of a 3D brain model 70 with mesh pattern and the target locations 74. FIG. 10B shows a side view of the 3D brain model 70 with avoidance region 76. For multiple targets 74, two symmetric points on the left and right hemispheres were used. For the avoidance region 76, part of the auditory cortex was used.

5. Brain Model Results

The performance of the optimization method of the present description was tested and compared to various state-of-the-art methods, including: single small electrode, ring pattern, maximum intensity, weighted least square (WLS), and LCMV. The same safety limits (including total current and current for individual electrode) were applied to the three optimization methods: WLS, LCMV and the optimization method of the present description. For the other three methods that do not use optimization, only the total current was restricted. Additionally, the LCMV method and optimization method of the present description were also compared in the following cases: single target, multiple targets, and single target with an avoidance region.

FIG. 11A shows the resulting electrical field for the LCMV method and FIG. 11B shows the resulting electrical field for the optimization method of the present description. FIG. 12A shows the weighting for each electrode used for the LCMV method and FIG. 12B shows the weighting for each electrode used for the optimization method of the present description. The optimization method of the present description shows better intensity and focality than LCMV (and WLS—not shown). The single electrode and maximum intensity methods (not shown) had high intensity at the target, but the focality of the electrical field was very low. The ring configuration (not shown) had a relatively focal activation area around the target, but weak intensity compared to that on the temporal cortex.

For one single prominent target, the optimization method of the present description performed better than LCMV in terms of intensity, directional intensity (DI), target error (TE) and focality.

For multiple targets, the two symmetric points 74 on the left and right hemispheres (FIG. 10A) were set to be the targets. While both methods were able to target both sites, and the focal accuracy is lower than that in the single target case. Compared to LCMV, the optimization method of the present description shows higher focal accuracy.

As illustrated in FIG. 10B, part of the auditory cortex is set to be the avoidance region 76. To avoid the auditory cortex, the activated area of LCMV shifted to the top, resulting in larger target error and lower focal accuracy. In comparison, the optimization method of the present description provides a more focal result with higher localization accuracy.

The influence of the electrode number on the focal accuracy of the stimulation was also studied. LCMV, maximum intensity and the optimization method of the present description were compared with electrode numbers of 21, 32 and 64. FIG. 13 shows a plot of the focality of LCMV method, maximum intensity method and the optimization method of the present description with different electrode number. One can see that as the electrode number increases, the focality improves. In particular, the optimization method of the present description provides the best focal accuracy.

In sum, the results showed that the optimization method of the present description is able to target any location with any orientation that is either specified by the user or provided by the EEG-brain imaging. It is able to deal with different complicated cases, such as single target, multiple targets, and target with avoidance region. It is worth noting that the result of single target is the best, since it has less constraints hence has a higher degree of freedom to select a better solution. Compared to the maximum intensity and LCMV methods, the optimization method of the present description maximizes the intensity and focality at the same time and achieves better focality and intensity. The benefits of the optimization method of the present description are especially significant when a certain region is not to be activated. The optimization method of the present description is able to avoid certain region without shifting the activated area too much, while the LCMV shifts the activation area, resulting in lower localization accuracy.

Results show that increasing electrode number helps to improve the stimulation. Therefore, an exemplary system may incorporate a dense multi-electrode array with up to 256 electrodes to achieve high stimulation precision. An exemplary configuration of an ultra-dense electrode array for brain imaging may be found in PCT International Application No. PCT/US2016/050452 filed on Sep. 6, 2016 and published as WO 2017/044433 A1 on Mar. 16, 2017, incorporated herein by reference in its entirety.

6. Internal Organ Stimulation

The methodology and procedures detailed above may also be applied to stimulate an internal organ (e.g., stomach, intestine, colon, spleen, or the like organ) noninvasively. The first step would be to construct a realistic 3D model for the internal organ (including other parts of torso outside of the internal organ) based on high-resolution structural images such as MRI and CT. In addition, a multiple electrode model on the skin should also be built in software such as but not limited to SolidWorks. Then the models can be imported into FEM software such as but not limited to COMSOL, where the models are meshed into large number of voxels, and the lead field matrix are calculated. After that, we can apply the same optimization methods to stimulate certain regions on the internal organ with high localization and focal accuracy. Concurrently, we can use the stimulation electrodes for recording purpose (same-electrode stimulation and recording) to provide feedback for the stimulation.

7. Hardware System

Commercially available or existing stimulators are bulky due to their implementation using off-the-shelf components and wired connections. In addition, they lack the capability of performing simultaneous stimulation and recording to unravel the complex dynamics beneath or adjacent to the stimulating electrode. To overcome the current limitations, the stimulation system 100 shown in FIG. 14 uses a miniaturized, versatile and flexible wireless stimulator (e.g., stimulator 200 shown in FIG. 17) in which each channel can be independently programmed.

In addition to the optimization algorithm, the key to a highly spatially focused direct current stimulation is enabling precise control of currents in each stimulation channel. Thus, the optimization algorithm detailed above may be used to its highest precision by providing a hardware platform as shown in stimulation system 100 of FIG. 14 that has the capability to enable this precision: a high channel-count stimulator with precise output current parameters for each channel and seemingly immediate dynamic updates to those parameters in real-time.

System 100 addresses these needs by offering an advantage of fast independent control of stimulation parameters for each of the electrodes 102 in stimulation array 104 (FIG. 14 shows 64 electrodes 102, however the array 104 may ideally use 256 or more electrodes), as well as simultaneous recording of neural signals from the same electrodes with a novel algorithm which allows immunity to stimulation artifacts that will otherwise corrupt the neural signals. In addition, the system 100 includes a two-way wireless data link 116, and a graphical user interface 118 to control the system wirelessly by means of a laptop, tablet or mobile phone, which also executes the optimization algorithms via application programming instructions for real-time stimulation configuration updates. All stimulator system 100 components are preferably integrated for ease of operation, and contain respective safety features allowing safe animal and human in-vivo testing.

The stimulator system 100 includes a stimulator System-On-Chip (SoC) 110, for implementation of a modulation system which supports the stimulator system 10. This SoC stimulator 110 is capable of driving stimulation current into electrode-tissue interfaces with wide ranges of impedance values. It is important to point out that high-density electrode implies smaller electrode size while small electrode inevitably results in higher electrode-tissue interface impedance. Thus, in order to accommodate this, special high voltage CMOS devices are employed as current sources in the design of the stimulator, resulting in the current driver's operating voltage range of +/−15V.

Another functional advantage of stimulator 110 is the capability for fast programming of each stimulation channel independently. The stimulator 110 includes supply regulators and a data receiver 122, and two layers of digital controllers on board, with one global controller 124 and multiple local controllers 128, both of which accepts data packets for stimulation configuration over a single input at a fast rate of 2 Mb/s. This in turn allows the ability to digitally program every channel with individual current settings at once within a few milliseconds of time. This capability is implemented to facilitate real-time updates to stimulation based on neural signal feedback and optimization algorithm during the stimulation session. The miniaturized form factor of the multi-channel stimulator chip 110 allows implementation of the stimulator system 10 in a compact packaging, usable for both clinical or personal (at home) applications.

One or more of the FPGA114, controller 124, or external processing device (e.g., tablet operating GUI 118) may comprise application programming 130 stored in memory 134 for executing the generating the optimized stimulation parameters and/or providing the stimulation commands delivered to the electrode array 104.

Moreover, the multi-channel stimulator SoC 110 may be configured to evoke a 2-D electric field pattern in-vitro (see FIG. 16 and Table 2). This is accomplished by selectively choosing the stimulation channels (e.g., channels 1, 9, 3 and 11 in FIG. 16), intensities, polarities, and return channel (electrode 6 in FIG. 16) in an the electrode array 104). FIG. 15 shows an image of recorded E-field from in-vitro stimulation using simultaneous multi-channel stimulation, as described above.

The on-board FPGA 114 (which may also be a microcontroller (MCU)) functions as the controller between recording amplifiers 106 (with multiplexer 108 and ADC 112), stimulator SoCs 110, and the wireless link 116. Custom firmware is included for an efficient communication of data packages between the components. The implementation of the two-way wireless link 116 and GUI software 118 leverage a neural interface approach. GUI 118 may also include a safety control which allows a single button stimulation turn off command. Finally, the full system 10 integrates the stimulator 110 and recording sections with a rechargeable battery (not shown) into a portable module with a form factor and size comparable to that of a smartphone. The software can be installed on a laptop or a mobile phone and use Bluetooth Low Energy (BLE) protocol to establish the two-way link with the hardware module at a rate of 240 kbps.

The technology previously described herein can be used to evaluate diseases associated with movement disorder (e.g., spinal cord injury, stroke, cerebral palsy, and Parkinson's disease) or regulation of the patient autonomic system (e.g., blood pressure, gastrointestinal motility, and inflammatory responses). For example, FIG. 17 shows a flow diagram for a method 150 for construction of a 3D spinal cord model. Due to the fact that the shape of human body varies from patient to patient, the stimulation parameters must be personalized to achieve optimal treatment efficacy without causing tissue damage. Building a 3D spinal cord model is thus a critical component for the use of the multi-electrode array to achieve high focality and intensity stimulation with optimized stimulation parameters using the methodology previously described herein. In the model construction, the patient first takes MRI/CT image at step 152 to derive his/her MRI/CT image. Subsequently, a mechanical model based on MRI/CT images is built at step 154, preferably including cerebrospinal fluid (CSF), spinal cord (gray and white matters), vertebrae, muscle, skin (e.g., stratum germ inativum and stratum corneum), as well as fat tissues. Each physical layer would then be assigned with corresponding electrical and thermal property (e.g., conductivity and permittivity) for simulation. Multi-physic simulation software (e.g., COMSOL) can, for example, be used to import the model for EM and thermal simulation to estimate the boundaries of safe stimulation parameters to avoid tissue damage. The 3D model from step 154 is incorporated in the optimization of the stimulation parameters at step 156, based on the set focality and intensity at the target or the set no-stimulation region in the spinal cord using the method previously described herein. This modeling flow can be used not only for spinal cord modeling, but also for the modeling of other organs of human body, such as brain, stomach, intestine, colon, nerves, heart, bladder, and so on. It is also not limited to transcutaneous electrical stimulation, but can be applied to other non-invasive or invasive neuromodulation scheme, such as focused ultrasound or implantable neural stimulator.

Conventional transcutaneous spinal cord stimulation stimulates the desired motor pool by placing the electrode on top of the vertebrae that covers the spinal cord segment of interest. For example, in order to stimulate L2 spinal segment, the electrode is often placed on-top-of T11-T12 vertebrae segments. However, the applied stimulation current is easily diverged from the target due to the irregular shape of the vertebrae. This means that the majority of the transcutaneously injected current flow to other undesired spinal cord segment and thus a high intensity stimulation current is required in order to elicit the response of the spinal cord. It is thus unnecessary and ineffective to place electrodes on top of the desired spinal segment and its corresponding vertebrae. Instead, the stimulation current can be effectively injected into the target spinal cord segment through the use of a transcutaneous multi-electrode array that delivers a combination of different parameters in each electrode. The weighting of the stimulation parameters can be calculated to focus on the segment or interests or to avoid the undesired segment using the described optimization model.

The systems and methods disclosed herein can also be used to stimulate the spinal cord ganglion with high selectivity, and is applicable to disease associated with movement disorder (e.g., Parkinson's disease, cerebral palsy, and stroke, and even traumatic brain injury) or stimulate sympathetic/non-sympathetic nervous systems.

FIG. 18 shows a schematic diagram of a transcutaneous multi-electrode array and stimulator system 200 in accordance with the present description. In a preferred embodiment, the electrode array and stimulator system 200 is configured to cover the entire or a portion of the spinal cord, including the ganglions and dorsal roots.

The stimulator system 200 comprises an electrode array 202 and controller/stimulator 208. The electrode array 202 comprises a flexible substrate 204 housing the array of electrodes 204, and is configured to be attached onto the patient's back through the 1) use of adhesive hydrogel and/or 2) one or multiple adjustable belts 206 that encircles the human chest or abdomen to fix the position of the electrode array. In the array, each electrode is replaceable and can be mounted/dismounted if necessary. One or multiple connectors 206 serve as the interface to link the electrode array 202 with the transcutaneous stimulator. In a preferred embodiment, the stimulator device 208 comprises multi-channel stimulation driver circuits and digital controller (e.g., stimulation shown in system 100 of FIG. 14) comprising a microprocessor, FPGA, CPU, VPU, and DSP, as well as memory (i.e. volatile or non-volatile memory) to store application programming in the form of instructions for executing pre-set or real-time received stimulation parameters on the microprocessor. The stimulator 208 may also comprise a control panel 210 allowing the user to selectively configure the parameters of each stimulation channel through the stimulator directly. System 250 may also include one or multiple corresponding connectors (e.g., connectors 206 in FIG. 18) from the stimulator link 116 (FIG. 14) the stimulator 208 and the electrode array 202 (FIG. 18) for the delivery of the stimulation current. The stimulator also comprises a power source (not shown) such as a rechargeable battery and a wireless module (e.g., Bluetooth and WiFi modules, not shown) for remote control and operation through a mobile device (not shown) hold by the patient or clinician.

The electrode array 202 comprises of N×M electrodes 204, where the number of the required electrodes varies with different patients and the targeted anatomical segments. Each electrode has a diameter ranging from 0.5 cm to 5 cm and spacing between 0.5 cm to 5 cm. Each electrode 204 may be individually replaceable, wherein the deteriorated electrode is removed and a new electrode is then inserted into the electrode array 202.

In one embodiment comprising transcutaneous spinal cord stimulation, the system 200 employs a multi-electrode array 202 with M (rows)*N (columns) electrodes. Here M varies from 1 to 100, and N varies from 1 to 100. The electrode array 202 generally has a total number varying from 2 to 1000, with diameter ranging between 50 μm and 8 cm. The electrode can have any shape, such as rectangular, circle, or ring. Note that the electrode 204 locations can also be customized, e.g., the electrode 204 arrangement does not need to be a rectangular array, but could be in other shapes or arrangements such as circular or occupying a freeform area. The current applied to each electrode 204 can be any value provided/calculated by the optimization algorithm, but should generally be lower than 250 mA, in order to meet the safety requirements. In addition, modulation waveforms can be provided to support neuromodulation by mixing two waveforms—e.g., low frequency signals (DC-300 Hz, sinusoidal, square mono-phasic, square biphasic, triangular) and high frequency signals (high frequency (1 kHz~40 kHz, sinusoidal, square mono-phasic, square biphasic, triangular). In the system of the present description, the electrode array is able to conduct concurrent recording and stimulation with the same electrode. The required number, location, and shape of the electrodes will be determined by the reconstructed spinal cord model and patient's body shape, multi-physic simulation, and the proposed optimization method.

In another embodiment comprising transcranial direct/alternating current stimulation, the disclosed system employs a multi-electrode array 202 that total 4~1000 electrodes 204, with diameter ranging from 0.1 cm~7 cm). For the electrode 204 location, any standard system locations (e.g., international 10-20, 10-10 or 10-5 system), or use customized locations can be used. The current applied to each electrode 204 may be any value provided/calculated by the optimization algorithm, but should generally be lower than 4 mA in order to meet safety requirements during constant direct current stimulation. However, one might also use a larger current (e.g., several to tens of mA) with a much shorter pulse width (e.g., 50 μs to 10 s of ms). As explained above, the electrode array is able to conduct concurrent recording and stimulation with the same electrode 204.

FIG. 19 shows a schematic diagram of a therapeutic spinal cord stimulation system 220 positioned on a patient, integrating the transcutaneous therapeutic spinal cord stimulator (e.g., stimulator 202 of FIG. 18 positioned on back of patient, not shown), vital sign sensors 224, and EMG sensors 226, as well as a wireless high-density brain recording system/stimulation 222 (i.e., EEG, ECoG or LFP/spike recordings). The therapeutic system 220 is preferably configured as not only a feedback, but also a feed-forward system. The vital sign sensor 224 carried by the patient may be configured to monitors the subject's heart rate, heart rate variation, EKG, EEG blood pressure/skin impedance, respiration rate, PPG, SpO2, blood pressure, EGG/ECoG, sweat, etc. are measured to ensure the safety of the stimulation and monitor the subject's condition. The vital sign sensor 224 is important, as spinal cord stimulation also modulates sympathetic and parasympathetic nerves that travel along with the spinal cord. Once an abnormal physiological signal is sensed, the stimulation parameters may be adapted or ceased. In another application, the spinal cord stimulation system can be used to regulate high blood pressure (BP) and the patent's BP can be sensed accordingly as a feedback control. In another application of using spinal cord stimulation to facilitate gastrointestinal (GI) motility, placing multiple sensors on the abdominal wall, can record electrogastrogram (EGG) to monitor GI motility.

In one embodiment, The signal from each wireless sensor 224/226 is synchronized and relayed to the stimulator system 200 or external storage (not shown) or the electronic health record of the hospital/clinics for feedback or feedward control, data analysis and remote patient monitoring.

The EMG sensors and accelerometers 226 are preferably deployed to the muscles of four limbs to sense both flexor and extensor muscle movements and the patients' postures during the system operation. The characteristics of EMG signals (i.e., the EMG intensity and firing patterns) and limb postures are used as important biomarkers for evaluating the effectiveness of the stimulation. Not only the early response of the EMG signal that appears right after stimulation, but also the middle and late EMG responses appearing several ms or up-to 100s of ms after stimulation are used to evaluate the efficacy of stimulation. It is also important to point out that different motor movements will generally require different stimulation parameters. For example, enabling walking and stepping of a paralyzed subject would use distinct stimulation parameters, and the parameters should be real-time adapted. The stimulator 200 would thus change its stimulation parameters adaptively based on the sensed EMG signals and patient's posture.

Brain signal recording serves as an important feed-forward control mechanism in the therapeutic system. Unlike conventional brain-computer interface or brain-machine-interface technology, recorded brain signals are directly used to trigger the actuator or served as trigger signal to stimulate the muscles. In the therapeutic system of the present description, the recorded brain signal is used to tune the parameters of spinal cord stimulation, (i.e. the activated electrode, stimulation frequencies, intensities, polarities, and pulse width). For instance, when the patient intends to climb the stairs, the recorded brain signal can be used to tune the stimulation patterns.

In some embodiments, the use of the system of the present description may be classified into two phases. In the first phase (the training phase), the patient/subject uses the device/system/software a couple of times per day to discover most efficacious stimulation parameters and stimulation spots, as well as learn of the operation of the system. In the second phase, the patient/subject wears the devices/system during their daily activities and sensors will collect the signal of interests as described previously for further analysis and processing.

FIG. 20 is a schematic block diagram of a wireless sensing and stimulation system/network 250 with a controller 208 configured to be held by the patient or the clinician. The controller 208 and stimulator 200 (or stimulator 100 of FIG. 14) are wirelessly coupled to multiple wireless sensors 226, and comprises a mobile device/App with GUI 210 designed for remote operation of the stimulator and wireless sensors 226. In addition to having the user control the stimulation through the stimulator 200 physically, the wireless controller 208 allows patient/clinician to configure the stimulator 200 and monitor the recorded physiological signals wirelessly. The recorded physiological signal is sent to either the stimulator 200 or the wireless controller 208 (e.g., tablet or like device) for signal analysis and the estimation of optimized stimulation parameters. Once there is a need to update or stop the stimulation parameters, new command is sent either through the stimulator 200 or the mobile device/App. of controller 208. The collected data will be eventually uploaded to cloud storage or can be sent to the electronic health record used in the hospital.

FIG. 21 is a schematic block diagram of a sensor network in accordance with the present description. In a preferred embodiment of the present description, the system may include multiple low-power wireless transceivers (226a through 226e) that support duplex data transmission (e.g., Bluetooth) for the sensor network implantation. Instead of connecting each wireless sensor to a common central hub, each sensor connects with each other. For example, $1^{st}$ sensor 226a transmits its recorded signal to the $2^{nd}$ sensor 226b. The $2^{nd}$ sensor 226b transmits its own-recorded signal along with signal derived from the $1^{st}$ sensor to $3^{rd}$ sensor 226c, and so on. The last sensor #n (226e, which may be one of the EMG sensors 226 or the vital sign sensor 224 shown in FIG. 19) collects all recorded physiological signals, e.g., #n–1 sensor 226d and all previous sensors, and transmits it to the stimulator 100/200 or remote control device 208. As an alternative method, each sensor can also connect to a central hop individually and the transmitted signal contains a time stamp information. The central hop then collects input from all sensors and synchronize all signals based on the timing information provided by each sensor.

Based on existing EM simulation results showing that the skin temperature can be elevated to induce skin burn due to the heat accumulated at the outermost skin layer that has highest resistivity, the duration of each stimulation/therapeutic session should be well controlled to avoid tissue damage and undesired side effects. If a patch-like planar or gel electrode is used for stimulation, each stimulation session should be limited to tens of minutes (e.g., 1-10 mins, 11-20 mins, 21-30 mins, 31-40 mins) to avoid skin burning and patient discomfort, while the separation between each stimulation/therapeutic session should be at least >1 minute. If the penetrating electrode is used, instead, to bypass the high-resistivity skin layer, (see PCT International Application No. PCT/US2016/063886 filed on Nov. 28, 2016 and published as WO 2017/091828 A1 on Jun. 1, 2017, herein incorporated by reference in its entirety), similar constraints should be applied to avoid unwanted side effects. The impedance of the electrode 204 should also be constantly monitored to ensure the robustness and reliability of both electrodes 204 and the stimulator 100/200. The impedance may be measured by measuring the peak voltage of the electrode overpotential induced by the known stimulation current. Moreover, the impedance between stimulation electrodes may also be carefully examined. As the device/system is designed for the daily use of patients/subjects, sweating would be an inevitable situation. Impedance between electrodes may therefore be measured to ensure there is no short circuit current flowing in between.

FIG. 22 shows a schematic diagram of a modulator 230 that modulates the stimulator output 232 and a modulation signal 236 specified by the user. In one embodiment, the modulator 230 comprises a signal mixer or a switch connected to the output of the stimulator 100/200. The stimulator output waveforms may be selected from low frequency signals (DC-300 Hz, sinusoidal, square mono-phasic, square bi-phasic, triangular signals) and high frequency signals (high frequency (1 kHz-40 kHz, sinusoidal, square monophasic, square biphasic, triangular signals), or the recorded electrophysiological signal waveforms (e.g., EMG, EKG, local field potential waveforms and action potential at its natural frequencies)

The user specifies the pulse width and separation of the modulation signal 234 to determine the number or the length of stimuli allowed to pass the mixer/switch per second. The number of allowable stimulation signals can range from 1 to 20,000 per second based on the efficacy of the treatment. The pulse separation can vary from 10 s to 0.001 s while the separation and pulse width between each adjacent pulse is adjustable and can be different to create a versatile and flexible stimulation waveform. This advantageously creates stimuli that comprises of a wide range of frequencies, which might help improve the treatment efficacy, as the physiological signal itself usually includes a wide range of frequencies.

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), formula(e), or computational depiction(s).

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, hardware processor, computer processor, central processing unit (CPU), and computer are used synonymously to denote a device capable of executing the instructions and communicating with input/output interfaces and/or peripheral devices, and that the terms processor, hardware processor, computer processor, CPU, and computer are intended to encompass single or multiple devices, single core and multicore devices, and variations thereof.

From the description herein, it will be appreciated that the present disclosure encompasses multiple embodiments which include, but are not limited to, the following:

1. A method for optimized transcutaneous stimulation of a target treatment region, the method comprising: generating a 3D model of the target treatment region as a function of an MRI or CT image of the target treatment region, a stimulation electrode array to be applied to the target treatment region, and calculation of a lead field matrix associated with the stimulation electrode array and the target treatment region; determining a safety limit for transcutaneous stimulation of the target treatment region; and generating an optimization model for stimulation parameters that provide both high intensity and focal accuracy within safety the safety limit by applying a parameter that assigns a weight to a directional intensity and focality associated with said transcutaneous stimulation; wherein said method is performed by a processor executing instructions stored on a non-transitory medium.

2. The method, apparatus or system of any preceding or subsequent embodiment, wherein generating a 3D model of the target treatment region comprises: acquiring the MRI or CT image of the target treatment region; segmenting the MRI or CT image into different tissues according to grey levels within the MRI or CT image; generating a target tissue model of the target treatment region for each of the different tissues; constructing an electrode model based on the stimulation electrode array and the constructed target tissue model; discretizing the target tissue model and electrode model into a large number of voxels to form a finite element model; and calculating a lead field matrix of the finite element model.

3. The method, apparatus or system of any preceding or subsequent embodiment, wherein the target treatment comprises the spine for optimization of transcutaneous spinal cord stimulation (tSCS).

4. The method, apparatus or system of any preceding or subsequent embodiment, wherein the target treatment comprises the brain for transcranial current stimulation (tCS).

5. The method, apparatus or system of any preceding or subsequent embodiment, wherein the target treatment comprises a region of the torso for internal organ stimulation.

6. The method, apparatus or system of any preceding or subsequent embodiment, wherein determining a safety limit is performed according to the function:

$$\begin{cases} |x_i| \le I_{max}, i = 1, \ldots, N \\ \sum_{i=1}^{N} |x_i| \le 2 * I_{total} \\ \sum_{i=1}^{N} x_i = 0 \\ Intensity_{avoid} \le \dfrac{1}{ratio} Intensity_{target} \end{cases} ;$$

wherein $I_{max}$ represents a maximum current at each electrode, $I_{total}$ denotes a maximum total injected current, and ratio represents an intensity ratio between the target treatment region and an avoidance region.

7. The method, apparatus or system of any preceding or subsequent embodiment, wherein generating an optimization model is performed according to:

$$x_{proposed} = \arg\min_{x} \frac{1}{w} \|Kx\|_2^2 - \lambda * e_0^T Cx$$

$$\text{subject to } \begin{cases} |x_i| \le I_{max}, i = 1, \ldots, N \\ \sum_{i=1}^{N} |x_i| \le 2 * I_{total} \\ \sum_{i=1}^{N} x_i = 0 \\ Intensity_{avoid} \le \dfrac{1}{ratio} Intensity_{target} \end{cases}$$

wherein w is a constant equal to a ratio between a total number of voxels and a number of targeted voxels; wherein $$\arg\min_{x} \frac{1}{w} \|Kx\|_2^2$$

applies the focality and $\lambda * e_0^T Cx$ applies to the directional intensity; and wherein $\lambda$ is the parameter that assigns a weight to a directional intensity and focality.

8. The method, apparatus or system of any preceding or subsequent embodiment: wherein by varying $\lambda$, an upper bound of focality and directional intensity can be estimated; and wherein directional intensity increases as $\lambda$ increases and focality increases as $\lambda$ decreases.

9. The method, apparatus or system of any preceding or subsequent embodiment, further comprising: performing EEG/EMG inverse image guided optimal stimulation to the target treatment region with the stimulation electrode array.

10. The method, apparatus or system of any preceding or subsequent embodiment, wherein the stimulation parameters provide direct current stimulation for focalized stimulation of the target tissue region at any orientation with high precision.

11. The method, apparatus or system of any preceding or subsequent embodiment, wherein multiple targets within the target region can be simultaneously stimulated or designated regions within the target tissue region can be avoided.

12. An apparatus for optimized transcutaneous stimulation of a target treatment region, the apparatus comprising: (a) a processor; and (b) a non-transitory memory storing instructions executable by the processor; (c) wherein said instructions, when executed by the processor, perform steps comprising: (i) generating a 3D model of the target treatment region as a function of an MRI or CT image of the target treatment region, a stimulation electrode array to be applied to the target treatment region, and calculation of a lead field matrix associated with the stimulation electrode array and the target treatment region; (ii) generating an optimization model for stimulation parameters that provide both high intensity and focal accuracy within safety the safety limit by applying a parameter that assigns a weight to a directional intensity and focality associated with said transcutaneous stimulation; and (iii) determining a safety limit for transcutaneous stimulation of the target treatment region.

13. The method, apparatus or system of any preceding or subsequent embodiment, wherein generating a 3D model of the target treatment region comprises: acquiring the MRI or CT image of the target treatment region; segmenting the MRI or CT image into different tissues according to grey levels within the MRI or CT image; generating a target tissue model of the target treatment region for each of the different tissues; constructing an electrode model based on the stimulation electrode array; discretizing the target tissue model and electrode model into a large number of voxels to form a finite element model; and calculating a lead field matrix of the finite element model.

14. The method, apparatus or system of any preceding or subsequent embodiment, wherein the target treatment comprises the spine for optimization of transcutaneous spinal cord stimulation (tSCS).

15. The method, apparatus or system of any preceding or subsequent embodiment, wherein the target treatment comprises the brain for transcranial current stimulation (tCS).

16. The method, apparatus or system of any preceding or subsequent embodiment, wherein the target treatment comprises a region of the torso for internal organ stimulation.

17. The method, apparatus or system of any preceding or subsequent embodiment, wherein determining a safety limit is performed according to the function $$\begin{cases} |x_i| \leq I_{max}, i = 1, \ldots, N \\ \sum_{i=1}^{N} |x_i| \leq 2 * I_{total} \\ \sum_{i=1}^{N} x_i = 0 \\ Intensity_{avoid} \leq \frac{1}{ratio} Intensity_{target} \end{cases};$$

wherein $I_{max}$ represents a maximum current at each electrode, $I_{total}$ denotes a maximum total injected current, and ratio represents an intensity ratio between the target treatment region and an avoidance region.

18. The method, apparatus or system of any preceding or subsequent embodiment, wherein generating an optimization model is performed according to:

$$x_{proposed} = \arg\min_{x} \frac{1}{w} \|Kx\|_2^2 - \lambda * e_0^T C x$$

$$\text{subject to} \begin{cases} |x_i| \leq I_{max}, i = 1, \ldots, N \\ \sum_{i=1}^{N} |x_i| \leq 2 * I_{total} \\ \sum_{i=1}^{N} x_i = 0 \\ Intensity_{avoid} \leq \frac{1}{ratio} Intensity_{target} \end{cases}$$

wherein w is a constant equal to a ratio between a total number of voxels and a number of targeted voxels; wherein $$\arg\min_{x} \frac{1}{w} \|Kx\|_2^2$$

applies the focality and $\lambda * e_0^T C x$ applies to the directional intensity; and wherein $\lambda$ is the parameter that assigns a weight to a directional intensity and focality.

19. The method, apparatus or system of any preceding or subsequent embodiment: wherein by varying $\lambda$, an upper bound of focality and directional intensity can be estimated; and wherein directional intensity increases as $\lambda$ increases and focality increases as $\lambda$ decreases.

20. The method, apparatus or system of any preceding or subsequent embodiment, wherein said instructions when executed by the processor further perform steps comprising: performing EEG/EMG inverse image guided optimal stimulation to the target treatment region with the stimulation electrode array.

21. The method, apparatus or system of any preceding or subsequent embodiment, wherein the stimulation parameters provide direct current stimulation or alternative current stimulation at a short period of time for focalized stimulation of the target tissue region at any orientation with high precision.

22. The method, apparatus or system of any preceding or subsequent embodiment, wherein multiple targets within the target region can be simultaneously stimulated or a designated region within the target tissue region can be avoided.

23. The method, apparatus or system of any preceding or subsequent embodiment, further comprising: a multi-electrode array comprising a network of high-density electrodes;

and a stimulator comprising high voltage CMOS/BJT devices that are employed as current sources; the stimulator comprising a global controller and a plurality of local controllers, both the global controller and plurality of local controllers being configured to accept data packets for a stimulation configuration over a single input.

24. The method, apparatus or system of any preceding or subsequent embodiment, the stimulator further configured to simultaneously and digitally program each electrode channel simultaneously.

25. The method, apparatus or system of any preceding or subsequent embodiment, the stimulator further configured to evoke a 2-D electric field pattern in-vitro by selectively choosing the stimulation channels, intensities, polarities, and return channel from selected electrodes within the electrode array.

26. A system for optimized transcutaneous stimulation of a target treatment region, the system comprising: (a) a multi-electrode array comprising a network of high-density electrodes; (b) a stimulator configured to control operation of the multi-electrode array; (c) a processor; and (d) a non-transitory memory storing instructions executable by the processor; (e) wherein said instructions, when executed by the processor, perform steps comprising; (i) generating a 3D model of the target treatment region as a function of an MRI or CT image of the target treatment region, a stimulation electrode array to be applied to the target treatment region, and calculation of a lead field matrix associated with the stimulation electrode array and the target treatment region; (ii) generating an optimization model for stimulation parameters that provide both high intensity and focal accuracy within safety the safety limit by applying a parameter that assigns a weight to a directional intensity and focality associated with said transcutaneous stimulation; and (iii) determining a safety limit for transcutaneous stimulation of the target treatment region; and (iv) performing EEG/EMG inverse image guided optimal stimulation to the target treatment region with the stimulation electrode array.

27. The method, apparatus or system of any preceding or subsequent embodiment, wherein generating a 3D model of the target treatment region comprises: acquiring the MRI or CT image of the target treatment region; segmenting the MRI or CT image into different tissues according to grey levels within the MRI or CT image; generating a target tissue model of the target treatment region for each of the different tissues; constructing an electrode model based on the stimulation electrode array; discretizing the target tissue model and electrode model into a large number of voxels to form a finite element model; and calculating a lead field matrix of the finite element model.

28. The method, apparatus or system of any preceding or subsequent embodiment, wherein the target treatment comprises the spine for optimization of transcutaneous spinal cord stimulation (tSCS).

29. The method, apparatus or system of any preceding or subsequent embodiment, wherein the target treatment comprises the brain for transcranial current stimulation (tCS).

30. The method, apparatus or system of any preceding or subsequent embodiment, wherein the target treatment comprises the region of the torso for internal organ stimulation.

31. The method, apparatus or system of any preceding or subsequent embodiment, wherein determining a safety limit is performed according to the function $$\begin{cases} |x_i| \le I_{max}, i = 1, \ldots, N \\ \sum_{i=1}^{N} |x_i| \le 2 * I_{total} \\ \sum_{i=1}^{N} x_i = 0 \\ Intensity_{avoid} \le \dfrac{1}{ratio} Intensity_{target} \end{cases};$$

wherein $I_{max}$ represents a maximum current at each electrode, $I_{total}$ denotes a maximum total injected current, and ratio represents an intensity ratio between the target treatment region and an avoidance region.

32. The method, apparatus or system of any preceding or subsequent embodiment, wherein generating an optimization model is performed according to:

$$x_{proposed} = \arg\min_x \frac{1}{w} \|Kx\|_2^2 - \lambda * e_0^T Cx$$

$$\text{subject to } \begin{cases} |x_i| \le I_{max}, i = 1, \ldots, N \\ \sum_{i=1}^{N} |x_i| \le 2 * I_{total} \\ \sum_{i=1}^{N} x_i = 0 \\ Intensity_{avoid} \le \dfrac{1}{ratio} Intensity_{target} \end{cases}$$

wherein w is a constant equal to a ratio between a total number of voxels and a number of targeted voxels; wherein $$\arg\min_x \frac{1}{w} \|Kx\|_2^2$$

applies the focality and $\lambda * e_0^T Cx$ applies to the directional intensity; and wherein $\lambda$ is the parameter that assigns a weight to a directional intensity and focality.

33. The method, apparatus or system of any preceding or subsequent embodiment: wherein by varying $\lambda$, an upper bound of focality and directional intensity can be estimated; and wherein directional intensity increases as $\lambda$ increases and focality increases as $\lambda$ decreases.

34. The method, apparatus or system of any preceding or subsequent embodiment, wherein the stimulation parameters provide direct current stimulation for focalized stimulation of the target tissue region at any orientation with high precision.

35. The method, apparatus or system of any preceding or subsequent embodiment, wherein multiple targets within the target region can be simultaneously stimulated or a designated region within the target tissue region can be avoided.

36. The method, apparatus or system of any preceding or subsequent embodiment, wherein the stimulator comprises a global controller and a plurality of local controllers, both the global controller and plurality of local controllers being configured to accept data packets for a stimulation configuration over a single input.

37. The method, apparatus or system of any preceding or subsequent embodiment, the stimulator further configured to simultaneously and digitally program each electrode channel simultaneously.

38. The method, apparatus or system of any preceding or subsequent embodiment, the stimulator further configured to evoke a 2-D or 3-D electric field pattern in-vitro by selectively choosing the stimulation channels, intensities, polarities, and return channel from selected electrodes within the electrode array.

39. The method, apparatus or system of any preceding or subsequent embodiment, wherein the return electrode is selected from a single or a subset of the electrodes in the array or by placing a return on an opposing side of the target tissue region.

40. The apparatus of any preceding or subsequent embodiment, the stimulator configured for generating a stimulation waveform by mixing at least waveforms from among low frequency signals, high frequency signals or the electrophysiological signal waveforms.

41. The method, apparatus or system of any preceding or subsequent embodiment, wherein the size of the electrodes ranges from 0.5 cm to 5 cm and the spacing between each electrode ranges from 0.5 cm to 5 cm.

42. The apparatus or method comprising using optimization techniques to improve the focal accuracy of transcutaneous spinal cord stimulation (tSCS), transcranial current stimulation (tCS), or internal organ stimulation.

43. The method, apparatus or system of any preceding or subsequent embodiment, wherein high intensity and focality of a target is achieved.

44. A method for optimizing stimulation parameters for transcutaneous spinal cord stimulation (tSCS), the method comprising: (a) determining a safety limit for transcutaneous spinal cord stimulation according to $$\begin{cases} |x_i| \leq I_{max}, i = 1, \ldots, N & (1) \\ \sum_{i=1}^{N} |x_i| \leq 2 * I_{total} & (2) \\ \sum_{i=1}^{N} x_i = 0 & (3) \\ Intensity_{avoid} \leq \frac{1}{ratio} Intensity_{target} & (4) \end{cases}$$

where $I_{max}$ represents the maximum current at each electrode, $I_{total}$ denotes the maximum total current injected to the body, and ratio represents the intensity ratio between the target and avoidance region; (b) developing an optimization model that always provides a feasible solution, which provides both high intensity and focal accuracy within safety constraints according to $$x_{proposed} = \arg\min_{x} \frac{1}{w} \|Kx\|_2^2 - \lambda * e_0^T Cx$$

$$\text{subject to } \begin{cases} |x_i| \leq I_{max}, i = 1, \ldots, N \\ \sum_{i=1}^{N} |x_i| \leq 2 * I_{total} \\ \sum_{i=1}^{N} x_i = 0 \\ Intensity_{avoid} \leq \frac{1}{ratio} Intensity_{target} \end{cases}$$

where the constant w is equal to the ratio between the total number of voxels and the number of targeted voxels, where the first term is the focality term and the second term is the intensity on the desired direction, and where the parameter $\lambda$ balances these two objectives and controls the relative importance of the focality and directional intensity; (c) performing EEG/EMG Inverse Image Guided Optimal Stimulation applied to transcutaneous spinal cord stimulation; and (d) using the foregoing to design optimal parameters for transcutaneous spinal cord stimulation to achieve focalized stimulation wherein any target location can be stimulated with any orientations with high precision, and wherein single or multiple targets can be stimulated and wherein designated regions can be avoided.

45. The method, apparatus or system of any preceding or subsequent embodiment, wherein the parameter $\lambda$ controls the relative importance between the intensity and the focality.

46. The method, apparatus or system of any preceding or subsequent embodiment, wherein by changing $\lambda$ an upper bound of focality and intensity is estimated.

47. The method, apparatus or system of any preceding or subsequent embodiment: wherein when $\lambda$ is very large, the best intensity results; and wherein when $\lambda$ is very small, the best focality results.

48. A method for optimizing stimulation parameters for transcranial current stimulation (tCS), the method comprising: (a) determining a safety limit for transcranial direct current stimulation according to $$\begin{cases} |x_i| \leq I_{max}, i = 1, \ldots, N & (1) \\ \sum_{i=1}^{N} |x_i| \leq 2 * I_{total} & (2) \\ \sum_{i=1}^{N} x_i = 0 & (3) \\ Intensity_{avoid} \leq \frac{1}{ratio} Intensity_{target} & (4) \end{cases}$$

where $I_{max}$ represents the maximum current at each electrode, $I_{total}$ denotes the maximum total current injected to the body, and ratio represents the intensity ratio between the target and avoidance region; (b) developing an optimization model that always provides a feasible solution, which provides both high intensity and focal accuracy within safety constraints according to $$x_{proposed} = \arg\min_{x} \frac{1}{w} \|Kx\|_2^2 - \lambda * e_0^T Cx$$

$$\text{subject to } \begin{cases} |x_i| \leq I_{max}, i = 1, \ldots, N \\ \sum_{i=1}^{N} |x_i| \leq 2 * I_{total} \\ \sum_{i=1}^{N} x_i = 0 \\ Intensity_{avoid} \leq \frac{1}{ratio} Intensity_{target} \end{cases}$$

where the constant w is equal to the ratio between the total number of voxels and the number of targeted voxels, where the first term is the focality term and the second term is the intensity on the desired direction, and where the parameter $\lambda$ balances these two objectives and controls the relative importance of the focality and directional intensity; (c)

performing EEG/EMG Inverse Image Guided Optimal Stimulation applied to transcranial current stimulation; and (d) using the foregoing to design optimal parameters for transcranial direct current stimulation to achieve focalized stimulation wherein any target location can be stimulated with any orientations with high precision, and wherein single or multiple targets can be stimulated and wherein designated regions can be avoided.

49. The method, apparatus or system of any preceding or subsequent embodiment, wherein the parameter $\lambda$ controls the relative importance between the intensity and the focality.

50. The method, apparatus or system of any preceding or subsequent embodiment, wherein by changing $\lambda$ an upper bound of focality and intensity is estimated.

51. The method, apparatus or system of any preceding or subsequent embodiment: wherein when $\lambda$ is very large, the best intensity results; and wherein when $\lambda$ is very small, the best focality results.

52. An apparatus for optimizing stimulation parameters for transcutaneous spinal cord stimulation (tSCS), the apparatus comprising: (a) a multi-electrode array; (b) a display device; (c) a hardware processor; (d) a non-transitory memory storing instructions executable by the hardware processor; (e) said instructions, when executed, performing steps comprising: (i) determining a safety limit for transcutaneous spinal cord stimulation according to $$\begin{cases} |x_i| \le I_{max}, i = 1, \ldots, N & (1) \\ \sum_{i=1}^{N} |x_i| \le 2 * I_{total} & (2) \\ \sum_{i=1}^{N} x_i = 0 & (3) \\ Intensity_{avoid} \le \frac{1}{ratio} Intensity_{target} & (4) \end{cases}$$

where $I_{max}$ represents the maximum current at each electrode, $I_{total}$ denotes the maximum total current injected to the body, and ratio represents the intensity ratio between the target and avoidance region; (ii) developing an optimization model that always provides a feasible solution, which provides both high intensity and focal accuracy within safety constraints according to $$x_{proposed} = \arg\min_{x} \frac{1}{w} \|Kx\|_2^2 - \lambda * e_0^T Cx$$

subject to $\begin{cases} |x_i| \le I_{max}, i = 1, \ldots, N \\ \sum_{i=1}^{N} |x_i| \le 2 * I_{total} \\ \sum_{i=1}^{N} x_i = 0 \\ Intensity_{avoid} \le \frac{1}{ratio} Intensity_{target} \end{cases}$ where the constant w is equal to the ratio between the total number of voxels and the number of targeted voxels, where the first term is the focality term and the second term is the intensity on the desired direction, and where the parameter $\lambda$ balances these two objectives and controls the relative importance of the focality and directional intensity; (iii) performing EEG/EMG Inverse Image Guided Optimal Stimulation applied to transcutaneous spinal cord stimulation; (iv) using the foregoing to design optimal parameters for transcutaneous spinal cord stimulation to achieve focalized stimulation wherein any target location can be stimulated with any orientations with high precision, and wherein single or multiple targets can be stimulated and wherein designated regions can be avoided; and (v) displaying stimulation information on the display device.

53. The method, apparatus or system of any preceding or subsequent embodiment, wherein the parameter $\lambda$ controls the relative importance between the intensity and the focality.

54. The method, apparatus or system of any preceding or subsequent embodiment, wherein by changing $\lambda$ an upper bound of focality and intensity is estimated.

55. The method, apparatus or system of any preceding or subsequent embodiment: wherein when $\lambda$ is very large, the best intensity results; and wherein when $\lambda$ is very small, the best focality results.

56. An apparatus for optimizing stimulation parameters for transcranial current stimulation (tCS), the apparatus comprising: (a) a multi-electrode array; (b) a display device; (c) a hardware processor; (d) a non-transitory memory storing instructions executable by the hardware processor; (e) said instructions, when executed, performing steps comprising: (i) determining a safety limit for transcranial direct current stimulation according to $$\begin{cases} |x_i| \le I_{max}, i = 1, \ldots, N & (1) \\ \sum_{i=1}^{N} |x_i| \le 2 * I_{total} & (2) \\ \sum_{i=1}^{N} x_i = 0 & (3) \\ Intensity_{avoid} \le \frac{1}{ratio} Intensity_{target} & (4) \end{cases}$$

where $I_{max}$ represents the maximum current at each electrode, $I_{total}$ denotes the maximum total current injected to the body, and ratio represents the intensity ratio between the target and avoidance region; (ii) developing an optimization model that always provides a feasible solution, which provides both high intensity and focal accuracy within safety constraints according to $$x_{proposed} = \arg\min_{x} \frac{1}{w} \|Kx\|_2^2 - \lambda * e_0^T Cx$$

subject to $\begin{cases} |x_i| \le I_{max}, i = 1, \ldots, N \\ \sum_{i=1}^{N} |x_i| \le 2 * I_{total} \\ \sum_{i=1}^{N} x_i = 0 \\ Intensity_{avoid} \le \frac{1}{ratio} Intensity_{target} \end{cases}$ where the constant w is equal to the ratio between the total number of voxels and the number of targeted voxels, where the first term is the focality term and the second term is the intensity on the desired direction, and where the parameter $\lambda$ balances these two objectives and controls the relative importance of the focality and directional intensity; (iii) performing EEG/EMG Inverse Image Guided Optimal Stimulation applied to transcranial current stimulation; (iv) using the foregoing to design optimal parameters for transcranial direct current stimulation to achieve focalized stimulation wherein any target location can be stimulated with any orientations with high precision, and wherein single or multiple targets can be stimulated and wherein designated regions can be avoided; and (v) displaying stimulation information on the display device.

57. The method, apparatus or system of any preceding or subsequent embodiment, wherein the parameter λ controls the relative importance between the intensity and the focality.

58. The method, apparatus or system of any preceding or subsequent embodiment, wherein by changing λ an upper bound of focality and intensity is estimated.

59. The method, apparatus or system of any preceding or subsequent embodiment: wherein when λ is very large, the best intensity results; and wherein when λ is very small, the best focality results.

60. An apparatus for non-invasive spinal cord stimulation for motility disorder, the apparatus comprising: a wireless controller; a stimulator; a plurality of wireless sensors; wherein said controller, said stimulator, and said wireless sensors are configured for: allowing a user to remotely operate the stimulator; allowing the user or a clinician to configure the stimulator and monitor the recorded physiological signals wirelessly; and receiving a recorded physiological signal that is sent to either the stimulator or the wireless control device for signal analysis and estimation of optimized stimulation parameters.

61. The method, apparatus or system of any preceding or subsequent embodiment: wherein the user first takes MRI to derive his/her MRI image; wherein a mechanical model based on MRI images is built, including cerebrospinal fluid (CSF), spinal cord (gray and white matters), vertebrae, muscle, skin (e.g., stratum germinativum and stratum corneum), as well as fat tissues; and wherein each physical layer is assigned a corresponding electrical and thermal property (e.g., conductivity and permittivity) for simulation.

62. The method, apparatus or system of any preceding or subsequent embodiment: wherein the stimulation parameters are adapted based on the physiological signals captured by sensors and the postures/motions the patient/subject intends to perform and the stimulation is ceased once abnormal vital signs are captured by the wireless sensors.

63. The method, apparatus or system of any preceding or subsequent embodiment: wherein the electrode for spinal cord stimulation is a planar electrode or needle electrode that penetrates dead skin to deliver electrical stimuli.

64. The method, apparatus or system of any preceding or subsequent embodiment, wherein the spinal cord stimulation system is used to modulate center/peripheral/autonomic nervous system, such as but not limited to motor function, brain state, GI motility, blood pressure, heart rate, and respiration rate As used herein, the singular terms "a," "an," and "the" may include plural referents unless the context clearly dictates otherwise. Reference to an object in the singular is not intended to mean "one and only one" unless explicitly so stated, but rather "one or more."

As used herein, the term "set" refers to a collection of one or more objects. Thus, for example, a set of objects can include a single object or multiple objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

| Conductivity Values Used For The 3D Spinal Cord Model | | |
|---|---|---|
| Electrical conductivity σ (S) | SC | 0.0018 |
| | SG | 0.15 |
| | Dermis | 1.62 |
| | Fat | 0.02383 |
| | Abdomen | 0.0414 |
| | Vertebrae | 0.0285 |
| | Muscle | 0.08 (transversal)/0.5 (longitudinal) |
| | CSF | 1.7 |
| | Gray matter | 0.023 |
| | White matter | 0.083 (transversal)/0.6 (longitudinal) |

TABLE 2

| Stimulator SoC Summary | |
| --- | --- |
| Max # of stimulation Channels | 256 |
| Out current per channel (effect # of channels: 256) | −0.5 to 0.5 mA |
| Out current per channel (effect # of channels: 64) | −2 to 2 mA |
| Stimulator compliance voltage | ±15 |
| Stimulator SoC size | 5.7 × 6.6 mm$^2$ |
| Static power consumption | 12 mW |

What is claimed is:

1. A method comprising:
receiving, by an external device comprising a processor, high-resolution structural images of a target treatment region of a patient, wherein a stimulation electrode array is placed within the target treatment region;
generating, by the external device, a 3D model based on high-resolution structural images of the target treatment region with the stimulation electrode array positioned within the target treatment region;
calculating, by the external device, based on the 3D model, a lead field matrix associated with the stimulation electrode array and the target treatment region;
determining, by the external device, a safety limit for transcutaneous stimulation of the target treatment region by the stimulation electrode array;
generating, by the external device, a set of parameters for a stimulation to be delivered by the stimulation electrode array based on the lead field matrix and the safety limit; and
communicating by the external device to the stimulation electrode array, the set of stimulation parameters, wherein the stimulation electrode array is configured to deliver a stimulation with high intensity and focal accuracy of electrical stimulation within the safety limit based on the set of stimulation parameters to the target treatment region,
wherein the set of stimulation parameters assigns a relative weight to directional intensity and focality of stimulation at the target treatment region.

2. The method of claim 1, wherein generating the 3D model further comprises:
segmenting the high-resolution structural images into different tissues according to grey levels;
generating a target tissue model of the target treatment region for each of the different tissues;
constructing an electrode model based on the stimulation electrode array and the constructed target tissue model; and
discretizing the target tissue model and electrode model into a large number of voxels to form a finite element model, wherein the lead field matrix is calculated based on the finite element model.

3. The method of claim 1, wherein the target treatment region comprises a spinal cord or spinal nerves.

4. The method of claim 1, wherein the target treatment region comprises a brain structure.

5. The method of claim 1, wherein the target treatment region comprises an internal organ.

6. The method of claim 1, wherein determining the safety limit for transcutaneous stimulation of the target treatment region by the stimulation electrode array further comprises determining a ratio between current to be applied to the target treatment region and to an avoidance region.

7. The method of claim 1, further comprising:
utilizing, by the external device, a stimulation optimization model to provide a feasible solution that includes both the high intensity and focal accuracy of electrical stimulation within the safety limit; and
wherein the stimulation optimization model is based on the focality of stimulation defining a ratio between the total number of voxels and the number of targeted voxels and the directional intensity of stimulation in the desired direction, wherein the focality and directional intensity of stimulation are balanced by assigning the relative weight terms.

8. The method of claim 1, further comprising:
measuring, by one or more sensing devices, one or more physiological signals, which includes at least one of EEG, EMG, EKG, EcoG, LFP, spike recording, accelerometer, PPG, SpO$_2$, respiration, or skin impedance signals;
adjusting, by the external device, one or more changes to the set of stimulation parameters in response to the measured physiological signals; and
generating, by the external device, an updated set of optimal stimulation parameters.

9. The method of claim 1, wherein the high-resolution structural images comprise MRI or CT images.

10. The method of claim 1, wherein the stimulation having the set of stimulation parameters provides direct current stimulation for focalized stimulation of the target treatment region at any orientation with high precision.

11. The method of claim 1, further comprising designating, simultaneously via the external device, at least one target within the target treatment region as a simulation target and at least one region within the target treatment region as a region to be avoided.

12. An apparatus comprising:
a stimulation electrode array configured to be placed within a target treatment region of a patient; and
an external device comprising:
a processor; and
a non-transitory memory storing instructions executable by the processor to perform steps comprising:
receiving high-resolution structural images of the target treatment region;
generating a 3D model based on the high-resolution structural images of the target treatment region with the stimulation electrode array placed within the target treatment region;
calculating, based on the 3D model, a lead field matrix associated with the stimulation electrode array and the target treatment region;
determining a safety limit for transcutaneous stimulation of the target treatment region by the stimulation electrode array;
generating a set of stimulation parameters to be delivered by the stimulation electrode array based on the lead field matrix and the safety limit; and
communicating to the stimulation electrode array the set of stimulation parameters, wherein the stimulation electrode array is configured to deliver a stimulation with high intensity and focal accuracy of electrical stimulation within the safety limit based on the set of stimulation parameters, where the set of stimulation parameters assigns a relative weight to a directional intensity and a focality of stimulation of the target treatment region.

13. The apparatus of claim 12, wherein the generating a 3D model further comprises:
segmenting the high-resolution structural images into different tissues according to grey levels;

generating a target tissue model of the target treatment region for each of the different tissues;

constructing an electrode model based on the stimulation electrode array and the constructed target tissue model; and discretizing the target tissue model and the electrode model into a large number of voxels to form a finite element model, wherein the lead field matrix is calculated based on the finite element model.

14. The apparatus of claim 12, wherein the high-resolution structural images comprise MRI or CT images.

15. The apparatus of claim 12, wherein the target treatment region comprises a spinal cord or spinal nerves, or a region of the brain.

16. The apparatus of claim 12, wherein the target treatment region comprises an internal organ.

17. The apparatus of claim 12, wherein the determining a safety limit for transcutaneous stimulation of the target treatment region by the stimulation electrode array further comprises determining a ratio between current to be applied to the target treatment region and to an avoidance region.

18. The apparatus of claim 12, wherein the instructions further perform one or more steps comprising:

utilizing a stimulation optimization model to provide a feasible solution that includes both the high intensity and focal accuracy of electrical stimulation within the safety limit, wherein the stimulation optimization model is based on the focality of stimulation defining a ratio between the total number of voxels and the number of targeted voxels and the directional intensity of stimulation in the desired direction, wherein the focality and directional intensity of stimulation are balanced by assigning the relative weight terms.

19. The apparatus of claim 12, wherein the instructions further perform steps comprising:

measuring one or more physiological signals using one or more sensors;

adjusting one or more changes to the set of stimulation parameters in response to the measured physiological signals; and generating an updated set of stimulation parameters.

20. The apparatus of claim 19, wherein said one or more physiological signals are selected from a group of physiological signals consisting of EEG, EMG, EKG, ECoG, LFP, spike recording, accelerometer, PPG, SpO2, respiration, and skin impedance signals.

21. The apparatus of claim 12, wherein the stimulation has a set of stimulation parameters that provide direct current stimulation or alternative current stimulation at a short period of time for focalized stimulation of the target tissue region at any orientation with high precision.

22. The apparatus of claim 12, wherein the instructions further perform steps comprising designating, simultaneously, at least one target within the target treatment region as a stimulation target and at least one region within the target treatment region as a region to be avoided.

23. The apparatus of claim 12:

wherein the stimulation electrode array comprises multiple stimulation electrodes; and wherein the external device provides independent stimulation signals to each of the multiple electrodes in the stimulation electrode array at a plurality of frequencies, intensities, and/or waveforms.

24. The apparatus of claim 12, further comprising:

one or more sensors selected from a group of physiological sensor consisting of sensors for EEG, EMG, EKG, ECoG, LFP, spike recording, accelerometer, PPG, SpO2, respiration, and skin impedance signals;

wherein the external device uses the one or more sensors for monitoring patient conditions, as well as for feedback control and/or feedforward control.

25. The apparatus of claim 23, wherein the independent stimulation signals are configured to evoke a 2-D electric field pattern in-vitro by selectively choosing the stimulation channels, intensities, polarities, and return channel of selected individual electrodes within the stimulation electrode array.

26. An apparatus comprising:

a stimulation electrode array configured to be placed within a target treatment region of a patient; and an external device comprising:

a processor; and a non-transitory memory storing instructions executable by the processor to perform steps comprising:

receive high-resolution structural images of the target treatment region;

generate 3D model based on the high-resolution structural images of the target treatment region with the stimulation electrode array placed within the target treatment region;

calculate, based on the 3D model, a lead field matrix associated with the stimulation electrode array and the target treatment region;

determine a safety limit for transcutaneous stimulation of the target treatment region by the stimulation electrode array; and generate a set of stimulation parameters to be delivered by the stimulation electrode array based on the lead field matrix and the safety limit by:

segmenting the high-resolution structural images into different tissues according to grey levels;

generating a target tissue model of the target treatment region for each of the different tissues;

constructing an electrode model based on the stimulation electrode array and the constructed target tissue model; and discretizing the target tissue model and the electrode model into a large number of voxels to form a finite element model, wherein the lead field matrix is calculated based on the finite element model; and communicate to the stimulation electrode array the set of stimulation parameters;

wherein the stimulation electrode array is configured to deliver a stimulation with high intensity and focal accuracy of electrical stimulation within the safety limit based on the set of stimulation parameters, where the set of stimulation parameters assigns a relative weight to a directional intensity and a focality of stimulation of the target treatment region.

* * * * *